United States Patent
Cales et al.

(10) Patent No.: US 9,996,671 B2
(45) Date of Patent: Jun. 12, 2018

(54) METHOD FOR PROVIDING RELIABLE NON-INVASIVE DIAGNOSTIC TESTS

(71) Applicants: UNIVERSITE D'ANGERS, Angers (FR); CENTRE HOSPITALIER UNIVERSITAIRE D'ANGERS, Angers (FR)

(72) Inventors: Paul Cales, Avrille (FR); Gilles Hunault, Angers (FR); Jerome Boursier, Angers (FR)

(73) Assignees: UNIVERSITE D'ANGERS, Angers (FR); CENTRE HOSPITALIER UNIVERSITAIRE D'ANGERS, Angers (FR)

( * ) Notice: Subject to any disclaimer, the term of this patent is extended or adjusted under 35 U.S.C. 154(b) by 561 days.

(21) Appl. No.: 14/413,445

(22) PCT Filed: Jul. 15, 2013

(86) PCT No.: PCT/EP2013/064954
§ 371 (c)(1),
(2) Date: Jan. 8, 2015

(87) PCT Pub. No.: WO2014/009569
PCT Pub. Date: Jan. 16, 2014

(65) Prior Publication Data
US 2015/0205928 A1    Jul. 23, 2015

(30) Foreign Application Priority Data

Jul. 13, 2012  (EP) ..................... 12176372

(51) Int. Cl.
| G01N 33/48 | (2006.01) |
| G06F 19/00 | (2018.01) |
| A61B 5/00 | (2006.01) |
| G01N 33/68 | (2006.01) |

(52) U.S. Cl.
CPC .......... *G06F 19/345* (2013.01); *A61B 5/4244* (2013.01); *A61B 5/746* (2013.01); *G01N 33/6893* (2013.01); *G06F 19/3431* (2013.01); *A61B 5/7221* (2013.01); *G01N 2800/085* (2013.01)

(58) Field of Classification Search
CPC .................................................... G06F 19/345
USPC .......................................................... 702/19
See application file for complete search history.

(56) References Cited

FOREIGN PATENT DOCUMENTS

| CN | 1968601 A | 5/2007 |
| CN | 101479599 A | 7/2009 |
| CN | 102334122 A | 1/2012 |
| WO | 01/86304 | 11/2001 |
| WO | 2004/058055 | 7/2004 |
| WO | 2005/116901 | 12/2005 |
| WO | 2006009702 A2 | 1/2006 |
| WO | 2007130831 A2 | 11/2007 |
| WO | 2010/013235 | 2/2010 |
| WO | 2010097472 A1 | 9/2010 |

OTHER PUBLICATIONS

Wai et al. "A simple noninvasive index can predict both significant fibrosis and cirrhosis in patients with chronic hepatitis C" Hepatology, 2003, 38(2):518-526.
Vallet-Pichard et al. "FIB-4: an inexpensive and accurate marker of fibrosis in HCV infection. Comparison with liver biopsy and fibrotest" Hepatology, 2007, 46(1):32-36.
Imbert-Bismut et al. "Biochemical markers of liver fibrosis in patients with hepatitis C virus infection: a prospective study" Lancet, 2001, 357(9262):1069-1075.
Rosenberg et al. "Serum markers detect the presence of liver fibrosis: a cohort study" Gastroenterology, 2004, 127(6):1704-1713.
Cales et al. "A novel panel of blood markers to assess the degree of liver fibrosis" Hepatology, 2005, 42(6):1373-1381.
Patel et al. "Evaluation of a panel of non-invasive serum markers to differentiate mild from moderate-to-advanced liver fibrosis in chronic hepatitis C patients" J. Hepatol., 2004, 41(6):935-942.
Leroy et al. "Prospective comparison of six non-invasive scores for the diagnosis of liver fibrosis in chronic hepatitis C" J. Hepatol., 2007, 46(5):775-782.
Boursier et al. "Improved diagnostic accuracy of blood tests for severe fibrosis and cirrhosis in chronic hepatitis C" Eur. J. Gastroenterol. Hepatol., 2009, 21(1):28-38.

(Continued)

*Primary Examiner* — Jerry Lin
(74) *Attorney, Agent, or Firm* — Young & Thompson

(57) ABSTRACT

Method for providing a reliable non-invasive diagnostic test of the presence and/or severity of a disease, and associated software and expert system includes:

a. collecting a diagnostic index, called Initial Index, preferably a score, b. calculating the Dispersion Index of the collected Initial Index, c. analyzing the reliability of each data by identifying if at least one data of index collected in step a) is an abnormal, inconsistent and/or a non-homogeneous data, or is responsible for a greater decrease in the Dispersion Index than that observed with other data, d. if a data is an abnormal, inconsistent and/or non-homogeneous data, or a data lowering a Dispersion Index, generating an Event Alert, e. if an Event Alert is generated, calculating new indexes, f. replacing the Initial Index including an abnormal, inconsistent and/or non-homogeneous data or a data affecting the Dispersion Index, with an Alternative, Estimated or a Mixed Index.

11 Claims, 6 Drawing Sheets

(56) References Cited

OTHER PUBLICATIONS

Cales et al. "Optimization and robustness of blood tests for liver fibrosis and cirrhosis" Clin. Biochem., 2010, 43(16-17):1315-1322.
Cales et al. "Comparison of blood tests for liver fibrosis specific or not to NAFLD" J. Hepatol., 2009, 50(1):165-173.
Adams et al. "Hepascore: an accurate validated predictor of liver fibrosis in chronic hepatitis C infection" Clin. Chem., 2005, 51(10):1867-1873.
Zarski et al. "Comparison of nine blood tests and transient elastography for liver fibrosis in chronic hepatitis C: the ANRS HCEP-23 study" J. Hepatol., 2012, 56(1):55-62.
Castera et al. "Prospective comparison of transient elastography, Fibrotest, APRI, and liver biopsy for the assessment of fibrosis in chronic hepatitis C" Gastroenterology, 2005, 128(2):343-50.
Ziol et al. "Noninvasive assessment of liver fibrosis by measurement of stiffness in patients with chronic hepatitis C" Hepatology, 2005, 41(1):48-54.
Stebbing et al. "A meta-analysis of transient elastography for the detection of hepatic fibrosis" J. Clin. Gastroenterol., 2010, 44(3):214-219.
Friedrich-Rust et al. "Performance of transient elastography for the staging of liver fibrosis: a meta-analysis" Gastroenterology, 2008, 134(4):960-974.
Delong et al. "Comparing the areas under two or more correlated receiver operating characteristic curves: a nonparametric approach" Biometrics, 1988, 44(3):837-845.
Hanley et al. "The meaning and use of the area under a receiver operating characteristic (ROC) curve" Radiology, 1982, 143(1):29-36.
International Search Report dated Nov. 19, 2013, corresponding to PCT/EP2013/064954.
Cales, et al.; "Evaluating the Accuracy and Increasing the Reliable Diagnosis Rate of Blood Tests for Liver Fibrosis in Chronic Hepatitis C"; vol. 28, No. 10; May 20, 2008; pp. 1352-1362.
Wang, et al.; "Identification of the Risk for Liver Fibrosis on CHB Patients Using Artificial Neural Network based on Routine and Serum Markers"; vol. 10, 251, Aug. 24, 2010; pp. 1-8.

METHOD FOR PROVIDING RELIABLE NON-INVASIVE DIAGNOSTIC TESTS

FIELD OF INVENTION

The present invention relates to a method for improving reliability of non-invasive diagnostic tests. More specifically, the present invention relates to a method for analyzing reliability of an Initial Index obtained by implementing a non-invasive test for assessing the presence and/or the severity of a disease, and for improving diagnosis accuracy of said test.

The method of the invention may apply for improving reliability of any non-invasive method for assessing the present diagnosis and/or the severity of a disease, and especially applies for liver diseases.

BACKGROUND OF INVENTION

Diagnostic of liver diseases may be performed through analysis of liver fibrosis. Liver fibrosis refers to the accumulation in the liver of fibrous scar tissue in response to injury of the hepatocytes due to various etiologies, such as for example infection with a virus (such as hepatitis viruses HCV and HBV), heavy alcohol consumption, toxins or drugs. The evolution of the fibrosis lesion may lead to cirrhosis, a condition in which the ability of the liver to function is impaired. Treatments of liver fibrosis exist, which can slow or halt fibrosis progression, and even reverse existing liver damages. On the contrary, cirrhosis is usually thought to be non-reversible.

Liver biopsy is the historical means implemented for diagnosing liver diseases in patients. Various classifications, based on liver biopsies, are used to grade fibrosis and cirrhosis, such as, for example, Metavir and Ishak (where cirrhosis is graded). For example, using Metavir scoring classification for fibrosis, five classes (named Metavir F stages) are distinguished: F0 (no fibrosis, no scarring), F1 (portal fibrosis, minimal scarring), F2 (few septa, scarring has occurred and extends outside the areas in the liver that contains blood vessels), F3 (many septa, bridging fibrosis is spreading and connecting to other areas that contain fibrosis) and finally F4 (cirrhosis or advanced scarring of the liver). In this patent application, any citation of F0, F1, F2, F3 and F4 is made with reference to the Metavir stages.

However, since liver biopsy is invasive and expensive, non-invasive diagnosis of liver fibrosis has gained considerable attention over the last 10 years as an alternative to liver biopsy. The first generation of simple blood fibrosis tests combined common indirect blood markers into a simple ratio, like APRI (Wai et al., Hepatology 2003) or FIB-4 (Valley-Pichard et al, Hepatology 2007). The second generation of calculated tests combined indirect and/or direct fibrosis markers by logistic regression, leading to a score, like Fibrotest™ (Imbert-Bismut et al., Lancet 2001), ELF score (Rosenberg et al., Gastroenterology 2004), FibroMeter™ (Cales et al., Hepatology 2005), Fibrospect™ (Patel et al., J Hepatol 2004), and Hepascore (Adams et al., Clin Chem 2005). For example, WO2005/116901 describes a non-invasive method for assessing the presence of a liver disease and its severity, by measuring levels of specific variables, including biological variables and clinical variables, and combining said variables into mathematical functions to provide a score, often called "fibrosis score".

However, these non-invasive diagnostic tests are not 100% accurate. Indeed, false-positive or false-negative results may occur, leading to patient misclassifications. Errors may primarily be attributed to the reference (liver biopsy) or to the construction of the test (as observed on academic data). Moreover, other sources of errors may arise from the measurement of markers or of physical data underlying the test, from the practitioner, or from the patient himself.

There is thus a need for a method for limiting the occurrence of patient misclassifications, and improving accuracy of non-invasive tests. An example of unefficacy of the prior art assumption for reliability of Fibroscan based on the AUROC is shown in Example 6: AUROCs of LSE in unreliable biopsies were not significantly different than in reliable biopsies.

WO2010/013235 describes a method for diagnosing a liver disease comprising computing a reliable score including data derived from a standard breath test and other parameters, such as, for example, physiological noise. Determining the physiological noise may include the use of an expert decision system. However, the method of WO2010/013235 is specific for a diagnostic test comprising performing a standard breath test, and cannot be adapted to other non-invasive diagnostic methods.

In Liver International ISSN1478-3223 (2008), pp 1352-1362, the Inventors published an article entitled "Evaluating and increasing the reliable diagnosis rate of blood tests for liver fibrosis in chronic hepatitis C". It is herein emphasized that reliability is a word that has different meanings in biostatistics. In this prior art document, the terms "reliable" or "reliability" was used to define reliable diagnostic intervals (RDI). RDI deals with a more precise diagnosis in terms of fibrosis stages. Thus, instead of a broad diagnosis of F2/F3/F4 stages (the patient is diagnosed as having a fibrosis, which is significant (F2) or advanced (F3) or cirrhotic (F4), one can obtain a RDI with F3/F4 diagnosis (the patient is diagnosed as having an advanced (F3) or cirrhotic (F4) fibrosis); in this prior art document, reliability refers to diagnostic precision.

In the present invention, reliability is not related to RDI. This invention is a method and an expert system for improving the reliability of a test, and cannot be used not for defining a RDI.

It is emphasized that in this invention, contrary to the prior art document, no RDI is defined; the reliability classes depict the patients groups with different accuracy levels defined by independent predictors of accuracy. For example, in patients with renal insufficiency a diagnostic test has a significantly lower accuracy than the same test in patients with normal renal function.

Also, it is emphasized that the dispersion index described in this invention is a new index of the value dispersion of a result, especially a score, comparable to standard deviation.

There is thus a need for a method for improving the reliability of diagnostic tests.

DEFINITIONS

In the present invention, the following terms have the following meanings:

"Liver disease" refers to an acute liver impairment, a chronic liver disease, a hepatitis viral infection especially an infection caused by hepatitis B, C or D virus, an hepatoxicity, a liver cancer, a steatosis, a non-alcoholic fatty liver disease (NAFLD), a non-alcoholic steatohepatitis (NASH), an autoimmune disease, a metabolic liver disease or a disease with secondary involvement of the liver.

According to an embodiment, hepatoxicity is alcohol induced hepatoxicity and/or drug-induced hepatoxicity (i.e. any hepatoxicity induced by a xenobiotic compound like alcohol or drug).

According to an embodiment, autoimmune disease is selected from the group consisting of autoimmune hepatitis (AIH), primary biliary cirrhosis (PBC) and primary sclerosing cholangitis (PSC).

According to another embodiment, metabolic liver disease is selected from the group consisting of NAFLD, hemochromatosis, Wilson's disease and alpha 1 anti-trypsin deficiency.

"Subject" refers to an animal. In one embodiment, the animal is a mammal, such as, for example, a rat or a pet, such as, for example, a cat or a dog. According to a preferred embodiment, the animal is a human.

According to an embodiment, the animal, including a human, is at risk of suffering or is suffering from a liver disease as hereinabove defined.

"Non-invasive diagnostic test" refers to a test for diagnosing, or for assessing the presence and/or severity of a disease may give a data, an index, or a score. Such test may use measurement of biomarkers, clinical markers, physical data (such as those obtained by the Fibroscan, for example), or scores. In one embodiment, a data may be a biomarker, a clinical marker, a physical data, an index or a score.

Examples of biomarkers include, but are not limited to, glycemia, total cholesterol, HDL cholesterol (HDL), LDL cholesterol (LDL), AST (aspartate aminotransferase), ALT (alanine aminotransferase), AST/ALT, AST.ALT, ferritin, platelets (PLT), AST/PLT, prothrombin time (PT) or prothrombin index (PI), hyaluronic acid (HA or hyaluronate), haemoglobin, triglycerides, alpha-2 macroglobulin (A2M), gamma-glutamyl transpeptidase (GGT), urea, bilirubin, apolipoprotein A1 (ApoA1), type III procollagen N-terminal propeptide (P3NP), gamma-globulins (GBL), sodium (Na), albumin (ALB), ferritine (Fer), Glucose (Glu), alkaline phosphatases (ALP), YKL-40 (human cartilage glycoprotein 39), tissue inhibitor of matrix metalloproteinase 1 (TIMP-1), TGF, cytokeratine 18 and matrix metalloproteinase 2 (MMP-2) to 9 (MMP-9), ratios and mathematical combinations thereof.

Examples of clinical markers include, but are not limited to, weight, body mass index, age, sex, hip perimeter, abdominal perimeter or height and the ratio thereof, such as for example hip perimeter/abdominal perimeter.

Examples of physical methods for assessing liver disease include, but are not limited to, medical imaging data and clinical measurements, such as, for example, measurement of spleen, especially spleen length. According to an embodiment, the physical method is selected from the group comprising ultrasonography, especially Doppler-ultrasonography and elastometry ultrasonography and velocimetry ultrasonography (preferred tests using said data are Fibroscan™, ARFI, VTE, supersonic imaging), MRI (Magnetic Resonance Imaging), and MNR (Magnetic Nuclear Resonance) as used in spectroscopy, especially MNR elastometry or velocimetry. Preferably, the data are Liver Stiffness Evaluation (LSE) data or spleen stiffness evaluation. According to a preferred embodiment of the invention, the data from physical methods are issued from a Fibroscan™. According to a preferred embodiment of the invention, measures or data issued from Fibroscan™ are one of the index involved in the method of the invention.

Examples of tests include, but are not limited to ELF, FibroSpect™, APRI, FIB-4, Hepascore, Fibrotest™, FibroMeter™, CirrhoMeter™, CombiMeter™, InflaMeter™.

ELF is a blood test based on hyaluronic acid, P3P, TIMP-1 and age.

FibroSpect™ is a blood test based on hyaluronic acid, TIMP-1 and A2M.

APRI is a blood test based on platelet and AST.

FIB-4 is a blood test based on platelet, ASAT, ALT and age.

HEPASCORE is a blood test based on hyaluronic acid, bilirubin, alpha2-macroglobulin, GGT, age and sex.

FIBROTEST™ is a blood test based on alpha2-macroglobulin, haptoglobin, apolipoprotein A1, total bilirubin, GGT, age and sex.

FIBROMETER™ and CIRRHOMETER™ together form to a family of blood tests, the content of which depends on the cause of chronic liver disease and the diagnostic target, and this blood test family is called FM family and detailed in Example 1.

COMBIMETER™ is a family of tests based on the mathematical combination of variables of the FM family (as detailed in Example 1) or of the result of a test of the FM family with FIBROSCAN™ result. In one embodiment, said mathematical combination is a binary logistic regression.

In one embodiment, the CombiMeter is a score based on the mathematical combination of physical data from liver or spleen elastometry such as dispersion index from Fibroscan™ such as IQR or IQR/median or median, preferably of Fibroscan™ median with at least 3, preferably at least 4, 5, 6, 7 or more and more preferably of 7 or 8 or 9 biomarkers and/or clinical data selected from the list comprising glycemia, total cholesterol, HDL cholesterol (HDL), LDL cholesterol (LDL), AST (aspartate aminotransferase), ALT (alanine aminotransferase), AST/ALT, AST.ALT, ferritin, platelets (PLT), AST/PLT, prothrombin time (PT) or prothrombin index (PI), hyaluronic acid (HA or hyaluronate), haemoglobin, triglycerides, alpha-2 macroglobulin (A2M), gamma-glutamyl transpeptidase (GGT), urea, bilirubin, apolipoprotein A1 (ApoA1), type III procollagen N-terminal propeptide (P3NP), gamma-globulins (GBL), sodium (Na), albumin (ALB), ferritine (Fer), Glucose (Glu), alkaline phosphatases (ALP), YKL-40 (human cartilage glycoprotein 39), tissue inhibitor of matrix metalloproteinase 1 (TIMP-1), TGF, cytokeratine 18 and matrix metalloproteinase 2 (MMP-2) to 9 (MMP-9), diabetes, weight, body mass index, age, sex, hip perimeter, abdominal perimeter or height and the ratio thereof ratios and mathematical combinations thereof.

In one embodiment, the CombiMeter is a score based on the mathematical combination of Fibroscan™ median with at least 3, preferably at least 4, 5, 6, 7 or more and more preferably of 7 or 8 or 9 biomarkers and/or clinical data selected from the list comprising alpha-2-macroglobulin (A2M), hyaluronic acid (HA), prothrombin index (PI), platelets (PLT), AST, Urea, GGT, Bilirubin (Bili), ALT, Ferritin, Glucose, age, sex and weight.

In one embodiment, CombiMeter™ results in a score based on the mathematical combination of Fibroscan™ median with platelets, PI, AST, HA, A2M, sex and age. In a preferred embodiment CombiMeter™ is a score based on the mathematical combination of Fibroscan™ median (liver stiffness) with a FibroMeter using the markers checked below:

| Cause | Age | Sex | Weight | A2M | HA | PI | PLT | AST | Urea | GGT | Bili | ALT | Fer | Glu | FS | $N^a$ | Ref |
|---|---|---|---|---|---|---|---|---|---|---|---|---|---|---|---|---|---|
| Virus | | | | | | | | | | | | | | | | | |
| FM V 2G | x | x | | x | x | x | x | x | | | | | | | | 8 | 2 |
| CM V 2G | x | x | | x | x | x | x | x | | | | | | | | 8 | 3 |
| FM V $3G^b$ | x | x | | x | x | | x | x | | x | | | | | | 8 | 4 |
| CM V $3G^b$ | x | x | | x | x | | x | x | | x | | | | | | 8 | 4 |

In one embodiment, CombiMeter™ results in a score based on the mathematical combination of Fibroscan™ median with platelets, PI, AST, HA, A2M, urea, ALT, sex and age.

In one embodiment, CombiMeter™ results in a score based on the mathematical combination of Fibroscan™ median with platelets, PI, AST, HA, A2M, urea, sex and age.

In one embodiment, CombiMeter™ results in a score based on the mathematical combination of Fibroscan™ median with platelets, PI, AST, HA, A2M, ALT, sex and age.

In one embodiment, CombiMeter™ results in a score based on the mathematical combination of Fibroscan™ median with PI, AST, A2M, diabetes and age.

In one embodiment, CombiMeter™ results in a score based on the mathematical combination of Fibroscan™ median with PI, AST/ALT, A2M, platelets, and diabetes.

In one embodiment, CombiMeter™ results in a score based on the mathematical combination of Fibroscan™ median with PI, HA, and A2M.

In another embodiment, CombiMeter™ results in a score based on the mathematical combination of Fibroscan™ median with a score of CirrhoMeter™, preferably a score of CirrhoMeter$^{2G}$.

In another embodiment, CombiMeter™ results in a score based on the mathematical combination of Fibroscan™ median with a score of FibroMeter™, preferably a score of FibroMeter$^{2G}$.

INFLAMETER™ is a companion test reflecting necro-inflammatory activity including ALT, A2M, PI, and platelets.

According to a preferred embodiment of the invention, at least one test of the FM family is involved in the method of the invention.

"Index" refers to any digit value obtained by a test for diagnosing, or for assessing the presence and/or severity of a disease, involving the mathematical combination of at least two data, preferably of at least two biomarkers, clinical markers and/or data resulting from physical method. In one embodiment of the invention, the mathematical combination is a linear combination of several markers (x, y, . . . ) like a +bx+cy (a, b, c . . . being the coefficients), preferably a binary logistic regression or a multiple linear regression. In one embodiment, an index is a digit value, preferably an unbound digit value. In one embodiment, a score is a bound digit value. In an embodiment, a score results from the transformation of an unbound index to a bound value by a mathematical function such as, for example, a logit function. Preferably, the score ranges from 0 to 1. In one embodiment, the data mathematically combined in an index, preferably in a score, are independent, i.e. give each an information that is different and not linked to the information given by the others. As known by one skilled in the art, implementing ELF, FibroSpect™ Hepascore, Fibrotest™, Fibro-Meter™, InflaMeter™, CirrhoMeter™, and CombiMeter™ results in a score with bound values whereas APRI and FIB-4 result in an index. According to the present invention, an index or a score may be the measurement of at least one biomarker, at least one clinical marker, at least one data resulting from a physical method for assessing liver disease and/or any mathematical combination thereof.

"Explained Data" corresponds to a data, an index or a score that has been obtained by implementing a non-invasive method for determining a disease. The Explained Data may be considered as a raw data. When the Explained Data is a score or an index, it is referred to as "Initial Index".

"Explanatory Data" corresponds to a data, an index or a score which is a reference data, index or score, used to assess reliability of an Explained Data. An Explanatory data may be the level of a data in a population of reference. An Explanatory Data may be an intrinsic or extrinsic data such as for example the expected data in the reference population or a reliability predictor.

"Final Index or Final Data": corresponds to the index or data resulting from the processing of the Initial Index or Explained Data respectively by the method of the invention. In one embodiment, the Final Index or Final Data refers to the last value of the diagnostic test result provided by the expert system to the practitioner. In one embodiment, if the expert system considers the Initial Index or the Explained Data as reliable, the Final Index or the Final Data is equal to the Initial Index or to the Explained data, respectively. In another embodiment, if the expert system considers the Initial Index or the Explained Data as unreliable, the Final Index or the Final Data is different from the Initial Index or from the Explained Data respectively (unless the difference is considered as non-significant). The Final Index or the Final Data may be considered as a processed data.

"Intrinsic Data": refers to data mathematically combined in a given test.

"Extrinsic Data": refers to a data which is not used in a given test for calculating the corresponding index.

"Accuracy": refers to the proportion of correctly classified patients by a diagnostic test.

"Analyzing the reliability of a test": means analyzing the reliability of a diagnostic test, wherein the reliability is the probability of a diagnostic test result to be accurate for an individual subject or a subgroup of subjects. Therefore, according to the invention, the reliability of the test is measured for an individual subject or for a subgroup of subjects, whereas the accuracy is measured for the whole population. In this patent application, not reliable, non-reliable and unreliable have the same meaning, i.e. indicate the probability of a diagnostic test result to be considered as non-accurate (accuracy <50%). In one embodiment of the invention, analyzing the reliability of a test corresponds to assessing the probability of error of diagnosis related to said test, i.e. checking the probability that the data resulting from said test may be erroneous. The more reliable a test is, the smaller the probability of error of classification is. Accordingly, the reliability may also correspond to the accuracy of the diagnosis in a patient subset, wherein the diagnostic accuracy refers to the percentage of patients with a correct diagnosis in the whole population.

"Checking the confidence of a data" means identifying abnormal data, inconsistent data and/or non-homogeneous data. In this patent application, not confident and non-confident have the same meaning when applied to a data, and refer to an abnormal, inconsistent or non-homogeneous data.

"Event alert": corresponds to an alert issued if a non-confident data or a non-reliable test is identified. An event alert triggers a response. In one embodiment, an event alert may also trigger the sending of an alert message or signal to the practitioner or to an expert physician.

"Expert System" refers to a computer system. In one embodiment, an expert system includes expert rules and automated analysis.

DETAILED DESCRIPTION

The present invention thus relates to a method for providing a reliable non-invasive diagnostic test resulting in an Explained Data, which is a data, an index or a score that has been obtained by implementing a non-invasive method for determining a disease, said method comprising:
a. collecting an Explained Data,
b. analyzing reliability of the Explained Data, and
c. providing the information whether or not the Explained Data is reliable, and if not reliable, providing a reliable Final Data.

In one embodiment, the method comprises:
a. collecting an Explained Data which means collecting the measurement of at least one, preferably at least two data selected from at least one biomarker, at least one clinical marker, at least one data resulting from a physical method for assessing the disease and/or at least one score or index,
b. analyzing reliability of the Explained Data which means analyzing the reliability of each data by identifying if a data collecting in step a. is an abnormal data, an inconsistent data; and/or a non-homogeneous data either with comparison to at least one Explanatory data, which may be an intrinsic or extrinsic data such as for example the expected data in the reference population or a reliability predictor; and/or by calculating the Dispersion Index,
c. providing the information whether or not the Explained Data is reliable, and if not reliable, replacing the Explained Data and providing a reliable Final Data.

In one embodiment of the invention, step c., i.e. providing the information whether or not the Explained Data is reliable, and if not reliable, providing a reliable Final Index includes:
a. generating an Event Alert whenever a data is non-confident and/or whenever an Explained Data is non-reliable according to its Explanatory Data or to reliability predictors; and when an Event Alert is issued, performing a preliminary analysis of the Event Alert,
b. triggering a response to the presence or the absence of event alert, which may be:
   i. the release the Explained Data as Final Data if no Event Alert occurred or remained after pretreatment or
   ii. the calculation and release of a Final Data more reliable than the Explained Data, together with a comment.

In one embodiment, the method of the invention includes:
identifying if a data is an abnormal data, and issuing an Event Alert which is an Abnormal Data Alert, and/or
identifying if a data is an inconsistent data and issuing an Event Alert which is an Inconsistent Data Alert, and/or
identifying if a data is a non-homogeneous data and issuing an Event Alert which is a Non-homogeneous Data Alert.

In one embodiment, the issued Event Alerts are treated, and the treatment comprises:
the suppression of one or more Event Alert(s), and/or
when several Event Alerts are issued, the prioritization of said Event Alerts to identify a main Event Alert.

In one embodiment of the invention, triggering the response comprises calculating new indexes, preferably new scores after Even Alert(s) are issued and pre-treated.

In one embodiment, collecting an Explained Data means collecting a diagnostic index, called Initial Index, preferably a score, more preferably a score selected from blood tests comprising ELF, FibroSpect™, APRI, FIB-4, Hepascore, Fibrotest™, or a score from the FibroMeter family, such as for example FibroMeter™ and CirrhoMeter™ or CombiMeter™; or a test derived from the FibroMeter Family, where urea was deleted from the markers; or another diagnostic test; said index involving the mathematical combination of at least two data, preferably of at least two biomarkers, clinical markers and/or data resulting from physical method; said index being referred to as Initial Index.

In one embodiment where the Explained Data is an Initial Index when one Event Alert is issued, at least one of the following new indexes is calculated:
an Alternative index, preferably an Alternative score, wherein the data having issued the Event Alert is suppressed, and/or
an Estimated index, preferably an Estimated score, wherein the data having issued the Event Alert is substituted by its central value, such as, for example, by its mean value.

In another embodiment where the Explained Data is an Initial Index, when at least two Event Alerts are issued, at least one of the following indexes, preferably scores, is calculated:
a Mixed index, preferably a Mixed score, wherein the data having issued the Main Event Alert is suppressed and the data having issued the Secondary Event Alert(s) is/are substituted their central value, such as, for example, by their mean values, and/or
an Estimated index, preferably an Estimated score, wherein all the data having issued the Event Alerts are substituted by their central value, such as, for example, by their mean values.

In one embodiment of the invention where the Explained Data is an Initial Index, triggering a response to said Event Alert(s) further comprises identifying the most reliable index, preferably score, among the initial index and the new indexes.

In one embodiment of the invention, Explanatory data is at least one reliability predictor. According to the invention, reliability predictors are selected from the group of data, called variables, included in or derived from non-invasive tests, as stated below, preferably FibroMeter™, InflaMeter™ and Fibroscan™, and more preferably urea, ALT, AST, score of CirrhoMeter$^{2G}$, score of FibroMeter$^{2G}$, Fibroscan™ classes, FibroMeter™ classes, CirrhoMeter™ classes, Fibroscan™ median, IQR, IQR/M, platelets, A2M, ratio urea/Fibroscan™ and Dispersion Index of the Initial Index.

In one embodiment, the Explained Data is an index or score ("Initial Index"), the Dispersion Index of the Initial Index is calculated and the reliability of each data included in the Initial Index is evaluated by its impact on a Dispersion Index. Evaluating the impact of a data on a Dispersion Index means performing a series of calculations of Dispersion Index of the Initial Index comprising n data where 1 to (n−2) data of the Initial Index are deleted, resulting in identifying and ranking the data lowering the most the Dispersion Index; the lowest Dispersion Index in the series indicates which data is to be deleted. The method of the invention includes thus this evaluation, and once the data are identified, the calculation of Alternative Indexes where the data lowering the Dispersion Index are deleted (triggered response).

In one embodiment, the method of the invention, for providing a reliable non-invasive diagnostic test of the presence and/or the severity of a disease, comprises:
 a. collecting a diagnostic index, called Initial Index, preferably a score, more preferably a score selected from blood tests comprising ELF, FibroSpect™, APRI, FIB-4, Hepascore, Fibrotest™, or a score from the FibroMeter family, such as for example FibroMeter™ and CirrhoMeter™ or CombiMeter™; or a test derived from the FibroMeter Family, where urea was deleted from the markers; or another diagnostic test; said index involving the mathematical combination of at least two data, preferably of at least two biomarkers, clinical markers and/or data resulting from physical method; said index being referred to as Initial Index,
 b. analyzing the reliability of each data by identifying if at least one data of index collected in step a) is an abnormal data, an inconsistent data; and/or a non-homogeneous data, or is the most decreasing the Dispersion Index than that observed with other data:
  i. with comparison of each data to the expected data in the reference population, or
  ii. with prediction of the index of step a) to intrinsic or extrinsic reliability predictor(s), or
  iii. by calculating the Dispersion Index of the Initial Index and then performing a series of calculations of Dispersion Index of the Alternatives Indexes corresponding to the Initial Index comprising n data where 1 to (n−2) data are deleted, resulting in identifying and ranking the data lowering the most the Dispersion Index,
  iv. by positioning the Index in a reliability class of the reliability classification based on the data obtained in a reference population,
 c. if a data is an abnormal, inconsistent and/or a non-homogeneous data, or a data lowering a Dispersion Index, generating an Event Alert,
 d. if an Event Alert is generated, if not already done, calculating new indexes, preferably new scores, said new indexes being:
  i. the same index as the Initial Index, but where the abnormal, inconsistent and/or a non-homogeneous data is suppressed (Alternative Index) or substituted by its central value, preferably its mean value (Estimated Index) or, if at least two data are abnormal, inconsistent or non-homogeneous, the most discordant is suppressed and the other(s) is/are substituted by its/their central value, preferably its/their mean value (Mixed Index), or
  ii. the index corresponding to Alternative Index where the data responsible for the lowest Dispersion Index is deleted,
 e. replacing the Initial Index comprising an abnormal, inconsistent and/or a non-homogeneous data or a data decreasing the Dispersion Index, with an Alternative Index, an Estimated Index, or a Mixed Index.

In an embodiment, the method of the invention comprises:
 collecting an index from the FibroMeter family, such as for example FibroMeter™ and CirrhoMeter™ or CombiMeter™; or a test derived from the FibroMeter Family, where urea was deleted from the markers; this index being referred to as Initial Index,
 calculating the Dispersion Index of the Initial Index collected in step a); identifying which is the data affecting the Dispersion Index, by performing a series of calculations of Dispersion Index of the Initial Index comprising n data where 1 to (n−2) data of the Initial Index are deleted,
 replacing the Initial Index comprising an Alternative index, where the data lowering the DI is/are deleted.

In an embodiment step c) is performed after having calculated if the Dispersion Index of the Initial Index corresponds to the ones of its of its intermediates deciles, preferably deciles 2-9, 2-8, 2-7, 3-9, 3-8, 3-7, 4-9, 4-8, 4-7, of the population of reference (deciles—10%—according to patient quantiles of Dispersion Index of the Initial Index).

In one embodiment of the invention, the test result is a score or an index, and the reliability of the test is analyzed in view of intrinsic data of said score or index. In a second embodiment of the invention, the test result is a score or an index and the reliability of the test is analyzed in view of extrinsic data (with or without intrinsic data).

[First Embodiment—ES2G]

In one embodiment, the present invention relates to a method for improving reliability of non-invasive diagnostic tests comprising:
 a1.—collecting the measurement of at least two data selected from at least one biomarker, at least one clinical marker, at least one data resulting from a physical method for assessing the disease and/or at least one score or index, and
 a2.—calculating an Initial Index (explained data) with the measurements or index or score collected in step (a), preferably by means of a test from the FibroMeter™ family, and
 b1.—checking the confidence of each data used in the test, and/or
 b2.—analyzing reliability of Initial index, for example in view of intrinsic data and/or in view of a reliability predictor,
 c1.—generating an event alert whenever a data is non-confident and/or whenever the Initial Index is non-reliable,
 d1.—triggering a response to said event alert, including providing a Final Index.

Collecting Data (Step a) and Calculating Initial Index (Step b)

In one embodiment, the method begins will collecting from a subject the measurement of at least two data selected from at least one biomarker, at least one clinical marker, at least one data resulting from a physical method for assessing the disease and/or a score or an index.

In this embodiment, advantageously, preferably at least 3 data, more preferably at least 4 data, and even more preferably at least 5 data are measured. In one embodiment of the invention, 2 data, preferably 3, 4, 5, 6, or 7 data or more are collected.

The at least two data are mathematically combined to obtain an index, preferably a score, more preferably a score selected from ELF, FibroSpect™, APRI, FIB-4, Hepascore, Fibrotest™, or a test from the FibroMeter family, such as for example FibroMeter™ and CirrhoMeter™ or CombiMeter™.

As this index is calculated before checking the confidence of each data, it is herein referred as Initial Index.

In this embodiment, the reliability of the test may be analyzed in view of intrinsic data of the index.

Identifying Abnormal Data, Inconsistent Data and/or Non-homogeneous Data.

Abnormal Data

As used herein, the term abnormal preceding the term data ("abnormal data") refers to a digit value which does not enter within the range of the usual digit values of this data measured in a reference population; an abnormal data generally results from a measurement error or from an erroneous recording.

In one embodiment, an abnormal data is smaller, preferable twice smaller, more preferably three times smaller and even more preferably 5 or 10 times smaller than the smallest expected data as measured in the reference population.

In another embodiment, an abnormal data is higher, preferably twice higher, more preferably three times higher, and even more preferably 5 or 10 times higher than the highest expected data as measured in the reference population.

In one embodiment, the reference population is a population of at least 500 subjects, preferably at least 1000 subjects. In one embodiment, the reference population comprises healthy subjects. In another embodiment, the reference population comprises non-healthy subjects, wherein said non-healthy subjects preferably have a liver disease. In another embodiment, the reference population comprises both healthy and non-healthy subjects.

Example 3 shows an example of data considered to be abnormal for some biomarkers and clinical data.

Inconsistent Data

As used herein, an "inconsistent data" is used with reference to an index, and is a data which is outside of the range of consistency for said data, measured as follows:
  arbitrarily fixing values for all data mathematically combined within said index, said arbitrarily fixing values being such that the result of the index is a high or a low value for this index. As an example, if the index is a score ranging from 0 to 1, the values of each data involved in the score are arbitrarily fixed to lead to a score ranging from 0.6 to 0.9, preferably of 0.7 or 0.8 (high value), or to lead to a score ranging from 0.1 to 0.4, preferably of 0.2 or 0.3 (low value),
  arbitrarily varying the value of one of the data, whereas the others are constant; and determining the influence of said variation on the index,
  fixing two "thresholds of influence" for said data, i.e. a high and a low threshold, corresponding to a value of the data considered as misleading, i.e. impacting the index in terms of reliability, i.e. putting the index at risk of giving a false positive or a false negative result.

According to the invention, a range of consistency of a data is index-dependent. For example, the range of consistency measured for the biomarker TIMP-1 within an ELF score may be different from the range of consistency of TIMP-1 within a FibroSpect™ score.

In one embodiment, the index is a score and the thresholds of influence are values of the data leading to a variation of the score of more than ±0.05, ±0.1, ±0.2, ±0.3 or ±0.35.

In diagnostic methods, when a score is measured, a score of 0 is usually indicative of the absence of the disease (or 0% probability or lack of diagnostic target), whereas a score of 1 represents the more severe form of the disease (or 100% probability or presence of diagnostic target).

Therefore, in one embodiment, a data leading to a decrease or to an increase of the score of more than 0.05, 0.1, 0.2, 0.3 or 0.35 when the other data used for this score calculation are arbitrarily fixed to lead to a low value, such as, for example, 0.2, or a high value, such as, for example, 0.8, may lead to false-negative or false-positive.

A false positive inconsistency is a data value resulting in a clinically significant positive (increase) deviation from the test result provided by the other data. For example, in an index including 8 markers, with a score result at 0.6 provided by 7 markers, the 8th marker will be the cause of a positive result if its input leads to a score result ≥0.75.

A false negative inconsistency is a data value resulting in a clinically significant negative (decrease) deviation from the test result provided by the other data. For example, in an index including 8 markers, with a score result at 0.6 provided by 7 markers, the 8th marker will be the cause of a negative result if its input provides a score result ≤0.45.

In both cases, the calculation of significant deviation for a marker/data is provided by simulations. Simulations are performed with different settings:
  Two score values: at a low (0.1 to 0.3) and a high (0.6 to 0.8) score value,
  Two degrees of significance for deviation: low and high significance, e.g. from 0.15 to <0.30 and ≥0.30, respectively, for a score from 0 to 1.

In one embodiment, the false-negative inconsistency range may be divided in several ranges, wherein the degree of the inconsistency increases. In one embodiment, the false negative inconsistency range may be divided in two ranges:
  a green zone, corresponding to values of the data leading to a negative (decrease) score deviation ranging from 0.15 to ≤0.30, when the values of other data used for score calculation are arbitrarily (preferably mimicking a clinically plausible setting) fixed to lead to a low score, such as, for example, a score of 0.3 and a high score, such as, for example, a score of 0.7, and
  a blue zone, corresponding to values of the data leading to a negative (decrease) score deviation ≥0.3, when the values of other data used for score calculation are arbitrarily fixed to lead to a low score, such as, for example, a score of 0.3 and a high score, such as, for example, a score of 0.7.

In one embodiment of the invention, a data of the green zone will be considered as less inconsistent than a data of the blue zone.

In one embodiment, the false-positive inconsistency range may be divided in several ranges, wherein the degree of the inconsistency increases. In one embodiment, the false positive inconsistency range may be divided in two ranges:
  a yellow zone, corresponding to values of the data leading to a positive (increase) score deviation ranging from 0.15 to ≤0.30, when the values of other data used for score calculation are arbitrarily fixed to lead to a low score, such as, for example, a score of 0.3 and a high score, such as, for example, a score of 0.7, and a red zone, corresponding to values of the data leading to a positive (increase) score deviation ≥0.3, when the values of other data used for score calculation are arbitrarily fixed to lead to a low score, such as, for example, a score of 0.3 and a high score, such as, for example, a score of 0.7.

In one embodiment of the invention, a data of the yellow zone will be considered as less inconsistent than a data of the red zone.

Example 3 shows an example of consistency ranges, false-positive inconsistency ranges and false-negative inconsistency ranges for some biomarkers and clinical data for FibroMeter™.

Non-Homogeneous Data

As used herein, a "non-homogeneous data" is a data which is non-homogeneous i.e. not concordant or not consistent with the other data measured in a test to calculate an index or a score.

In one embodiment, a data is considered non-homogeneous with others when the removal of said data leads to a 10% variation of the actual index (or score), more preferably of to a 20% variation, preferably to a 30% variation of the index (or score). If not, the data is considered homogeneous.

In another embodiment, a data is considered as non-homogeneous, when it is below the threshold of the dispersion index of said test, which is known or calculated by the skilled artisan. A data is considered as homogeneous, when it is above the threshold of the dispersion index of said test.

Dispersion Index

In one embodiment of the invention, the reliability of a test is checked by measuring the dispersion index (DI), of the data or tests used in the method (the measurement of biomarker(s), clinical marker(s), data resulting from a physical method for assessing the disease and/or any mathematical combination thereof).

The dispersion index is an index depicting the dispersion of said data, which, in an embodiment, are mathematically combined to obtain an index, for example the Initial Index. In one embodiment, when the index comprises the combination of n data, alternative diagnostic indexes using a mathematical combination of n−1 of these n data are measured to determine the dispersion index. A dispersion index of 1 (100%) corresponds to a perfect homogeneity of the data, and a dispersion index of 0 corresponds to total dispersion of data.

An index value is considered as unreliable when a dispersion threshold is reached. The dispersion threshold of DI is calculated thanks to the plot of DI against the absolute difference $\delta_1$ between initial and final index as defined above (as shown in the Example 2 and in FIG. 1).

For example, with FibroMeter$^{2G}$ the reliability threshold of DI is 0.81.

This invention thus shows that:
if the DI is over the dispersion threshold, (i.e. when data are homogeneous), the Initial Index is poorly impacted, which means that the Initial Index is reliable,
if the DI is under the dispersion threshold, the Initial index is not reliable and Alternative or Estimated Indexes are required.

In one embodiment, said dispersion index may be measured as follows:

X is a sample of n $x_i$ values of the index, wherein the values of the $x_i$ range from a to b; therefore $$RI = s(X)/s_m(a, b)$$

wherein s(X) is the empirical standard deviation of X and wherein $s_m(a, b)$ is the maximal empirical standard deviation on [a, b] for a sample comprising n values if n is odd, or n+1 values if n is even.

In one embodiment, when the dispersion index is used, the method of the invention comprises the following steps:
(a) the dispersion index is calculated as hereinabove described, by using all the n data mathematically combined in the index,
(b) threshold of the dispersion index is determined, behind which the rate of diagnostic test accuracy is significantly decreased,
(c) when this dispersion threshold is reached, the n alternative indexes (indexes corresponding to the mathematical combination of n−1 data as hereinabove described) are compared,
(d) the alternative index responsible for the largest change in dispersion index is determined, i.e. that with the most dispersed value compared to the Initial Index (or to the previous index for step f), and the data is excluded,
(e) a new dispersion index is calculated without the excluded data of step (d),
(f) if the dispersion threshold is still reached, steps (b) to (e) are repeated until the dispersion index threshold is not reached or until the number of remaining data is less than 4.

In one embodiment, for an index resulting from the combination of n data, the maximum number of excluded data is of less than or equal to n/3, preferably of less than or equal to n/4.

The initial or alternative index leading to a dispersion index that does not reach the dispersion threshold is considered as the Final Index.

Said Final index may thus be finally used for assessing the presence and/or the severity of a liver disease in the subject. In one embodiment, said assessment includes the classification of the subject in a class of a fibrosis stage classification, i.e. a class of a classification wherein each class is associated with a fibrosis stage, such as, for example, one or more Metavir F stage(s).

In one embodiment, the method of the invention comprises releasing a comment on reliability, including one of:
indicating the number of Event Alerts,
indicating the data having issued an Event Alert or the main Event Alert,
indicating which one of the data is/are excluded,
indicating the Final Index.

Event Alert

Types of Event Alert

According to an embodiment of the invention, an event alert is issued if a non-confident data is identified.

In one embodiment, said event alert may correspond to the identification of an abnormal data (Abnormal Data Alert), of an inconsistent data (Inconsistent Data Alert) and/or of a non-homogeneous data (Non-Homogeneous Data Alert).

In one embodiment, a data may generate both an Inconsistent Data Alert and a Non-Homogeneous Data Alert.

In one embodiment, according to the inconsistency ranges hereinabove described, an Inconsistency Data Alert may be:
a False-Positive Inconsistency Data Alert (if the data belongs to the false-positive inconsistency range), or
a False-Negative Inconsistency Data Alert (if the data belongs to the false-negative inconsistency range).

In one embodiment, a False-Positive Inconsistency Data Alert may be:

a Red Alert (if the data belongs to the red false-positive inconsistency zone), or a Yellow Alert (if the data belongs to the yellow false-positive inconsistency zone).

In one embodiment, a False-Negative Inconsistency Data Alert may be:

a Blue Alert (if the data belongs to the red false-negative inconsistency zone), or a Green Alert (if the data belongs to the yellow false-negative inconsistency zone).

Preliminary Analysis of Event Alerts

In one embodiment, a preliminary analysis of Event Alerts may be carried out before triggering a response to said event alert.

In one embodiment, said preliminary analysis may correspond to the suppression of an Event Alert (i.e. the data having issued the Event Alert is finally considered as reliable) or to the prioritization of said alerts, thereby defining a "main Event Alert" and "secondary Event Alert(s)".

Suppression of Event Alerts

In one embodiment, each data is considered separately: when one data generates an Inconsistent Data Alert but no Non-Homogeneous Data Alert, i.e. when the data is inconsistent but homogeneous with the other data mathematically combined within the index, the Inconsistent Data Alert is subsequently suppressed (i.e. do not lead to a score change). This embodiment is repeated for each data of the index.

In another embodiment of the invention, several data are considered simultaneously: when at least two, preferably at least three, more preferably at least four Data Inconsistency Alerts of the same type, i.e. 2 or 3 or 4 or more False-Positive or False Negative Inconsistency Data Alerts are simultaneously triggered, said Inconsistent Data Alerts may be subsequently suppressed (i.e. do not lead to a score change). In one embodiment of the invention, when at least two, preferably at least three, more preferably at least four Negative Inconsistency Data Alerts are simultaneously triggered, said Inconsistent Data Alerts are not suppressed.

One skilled in the art, in view of the above, is capable of drafting further rules for pre-treating data (such as, for example, suppressing a single Event Alert when a specific biomarker or clinical data (such as, for example, age, sex or ASAT) is involved; never suppressing False-Negative Inconsistency Data Alerts, and the like). Examples of such Rules when a FibroMeter™ is carried out are shown in Example 4.

Prioritization:

In one embodiment, if several Event Alerts are issued, a preliminary analysis comprising the prioritization of said alerts may be carried out, thereby defining a "main Event Alert" and "secondary Event Alert(s)".

Examples of Rules of preliminary analysis when several Inconsistent Data Alerts are issued are shown below:

a False-Positive Inconsistency Data Alert may be considered as more important (i.e. "main") than a False-Positive Inconsistency Data Alert (which therefore will be "secondary"), a Blue Alert may be more important than a Green Alert, a Red Alert may be more important than a Yellow Alert, if two similar Event Alerts are issued, such as, for example, two Blue Alerts, the main Alert may be the one issued by the data being the furthest from its central value like mean or with the greatest impact on score value, etc. . . .

Other examples of preliminary analysis rules of Event Alerts when FibroMeter™ is carried out are shown in Example 4.

New Indexes—Treatment of Data

In one embodiment of the invention, new indexes, preferably new scores, are calculated after Event Alerts are issued and pre-treated, if some Event Alerts subsist after said preliminary analysis.

In one embodiment, a single Event Alert is issued, and at least one of the following indexes, preferably scores, is calculated:

an Alternative index, preferably an Alternative score, wherein the data having issued the Event Alert is suppressed, and/or an Estimated index, preferably an Estimated score, wherein the data having issued the Event Alert is substituted by its central value, such as, for example, by its mean value.

In one embodiment, at least two Event Alerts are issued, and at least one of the following indexes, preferably scores, is calculated:

a Mixed index, preferably a Mixed score, wherein the data having issued the Main Event Alert is suppressed and the data having issued the Secondary Event Alert(s) is/are substituted by their central values like mean, and/or an Estimated index, preferably an Estimated score, wherein all the data having issued the Event Alerts are substituted by their central values, such as, for example, by their mean values.

In one embodiment of the invention, the mean value of a data corresponds to the mean value (preferably arithmetic mean) for said data measured in a reference population.

Triggered Response

In one embodiment of the invention, the response may be the release of the Initial Index as Final Index if no event alert remains after pretreatment or the calculation of new indexes, preferably new scores and the release of a Final Index different from the Initial Index (Alternative Index or Estimated Index), preferably together with a comment.

Selection of the Most Reliable Index

In one embodiment, a single Event Alert is issued and the selection of the most appropriate index is carried out by comparing the value of the Initial index (II) with the value(s) of the Alternative index (AI) and/or of the Estimated index (EI).

In one embodiment, if |II—AI| is superior to $\delta_2$, the AI is considered as the most reliable index, wherein $\delta_2$ is the clinically significant difference. In one embodiment, $\delta_2$ ranges from 0.05 to 0.3, preferably from 0.1 to 0.2, more preferably is about 0.15.

In one embodiment, if |II—AI| is inferior or equal to $\delta_2$, wherein $\delta_2$ is as hereinabove described, 6 situations are distinguished:

if II<Ct≤AI, AI is considered as the most reliable index; wherein Ct stands for Critical threshold, and corresponds to the cirrhosis threshold for the index, i.e. the digit value of said index leading to the classification of the subject in the cirrhosis or F4 Metavir stage, if AI≤Ct<II, AI is considered as the most reliable index; wherein Ct is as hereinabove described, if Ct≤II≤AI, AI is considered as the most reliable index; wherein Ct is as hereinabove described, if Ct≤AI≤II, AI is considered as the most reliable index; wherein Ct is as hereinabove described, if AI≤II≤Ct, II is considered as the most reliable index; wherein Ct is as hereinabove described, and if II≤AI≤Ct, II is considered as the most reliable index; wherein Ct is as hereinabove described.

In one embodiment of the invention, the test is a FibroMeter$^{1G}$, and Ct is of about 0.88.

In one embodiment, a least two Event Alerts are issued and the selection of the most appropriate index is carried out by comparing the value of the Initial index (II) with the value(s) of the Mixed index (MI) and/or of the Estimated index (EI).

In one embodiment, if|II—MI| is superior to $\delta_2$, the MI is considered as the most reliable index, wherein $\delta_2$ is the clinically significant difference. In one embodiment, ranges from 0.05 to 0.3, preferably from 0.1 to 0.2, more preferably is about 0.15.

In one embodiment, if |II—MI| is inferior or equal to $\delta_2$, wherein $\delta_2$ is as hereinabove described, 6 situations are distinguished:
  if II<Ct≤MI, MI is considered as the most reliable index; wherein Ct stands for Critical threshold, and corresponds to the cirrhosis threshold for the index, i.e. the digit value of said index leading to the classification of the subject in the cirrhosis or F4 Metavir stage,
  if MI≤Ct <II, MI is considered as the most reliable index; wherein Ct is as hereinabove described,
  if Ct≤II≤MI, MI is considered as the most reliable index; wherein Ct is as hereinabove described,
  if Ct≤MI≤II, MI is considered as the most reliable index; wherein Ct is as hereinabove described,
  if MI≤II≤Ct, II is considered as the most reliable index; wherein Ct is as hereinabove described, and
  if II≤MI≤Ct, II is considered as the most reliable index; wherein Ct is as hereinabove described.

In one embodiment of the invention, the test is a FibroMeter$^{1G}$, and Ct is of about 0.88.

In one embodiment of the invention, the selected index is called the Final index. Said index may thus be finally used for assessing the presence and/or the severity of a liver disease in the subject. In one embodiment, said assessment includes the classification of the subject in a class of a fibrosis stage classification, i.e. a class of a classification wherein each class is associated with a fibrosis stage, such as, for example, one or more Metavir F stage(s).

In one embodiment, the method of the invention comprises releasing a comment. In one embodiment, said comment comprises indicating the number of Event Alerts, and the data having issued an Event Alert or the main Event Alert. In one embodiment, said comment comprises indicating which one of the indexes has been considered as the most reliable one. In one embodiment, said comment comprises a warning message, wherein the more alerts there are, the more the result must be considered carefully.

[Second Embodiment—ES3G]

The present invention relates to a method for providing reliable diagnostic tests, comprising:
  a'1—collecting at least one, preferably at least two indexes or scores or physical data resulting from non-invasive tests implemented in a subject,
  b'1—analyzing the reliability of each index or score,
  c'1—generating an event alert if a test is non-reliable,
  d'1—triggering a response to said event alert.

Data

In this embodiment, in step a'1, preferably at least 2, 3, 4, 5 index or scores or physical data or more are measured. In one embodiment of the invention, said indexes or scores or physical data are preferably indexes, more preferably scores and/or physical data.

In one embodiment, the method of the invention comprises at least one score resulting from a test from the FibroMeter family and at least one physical data resulting from Fibroscan™. According to a specific embodiment, the collected result from FibroMeter™ (score), and Fibroscan™ (physical data) were obtained from the same subject within six months, preferably within two months.

Analyzing Reliability

In one embodiment, analyzing the reliability of a test means considering one data (score or physical data, in our embodiment) as the Explained Data while the other ones are Explanatory Data.

In this embodiment, the reliability of the test is analyzed in view of intrinsic and/or extrinsic data of the index.

Reliability Predictors

In an embodiment, the term score means score provided by logit function included in binary logistic regression where logit function: 1/1-eR with R=c+ax+by . . . . These scores provide independent reliability predictors. Consequently, they determine reliability classes with qualitative reliability descriptors from unreliable to very reliable diagnostic test result. Most results are based on the following diagnostic target: correctly diagnosed by detailed fibrosis classification unless otherwise stated (such as, for example, binary target and/or presence or absence).

Reliability Predictors without Segmentation (for the Whole Population)

Examples of reliability predictors are: the Dispersion Index of the score, AST, ALT, a score combining Dispersion Index and AST.

Reliability Predictors with Segmentation (for Subset of Patients)

For specific subsets of patients, examples of reliability predictors of a test (such as for example FIBROSCAN™, FIBROMETER™, CIRRHOMETER™, COMBIMETER™) are: the FIBROSCAN™ median); FIBROSCAN™ classifications, IQR/M, IQR, FIBROMETER™ classification, CIRRHOMETER™ classification, urea, ALT, AST, score of CirrhoMeter$^{2G}$, score of FibroMeter$^{2G}$; in a reliability predictors may be defined a threshold for negative predictive values; and another threshold for positive predictive values In one embodiment, the reliability analysis comprises two steps:
  the first step corresponds to the calculation of ranked probabilities determining reliability classes. For example, when a majority of subject results in a subject subgroup are misclassified, the result is considered as unreliable. In one embodiment, when the probability or frequency of accurate results is ≥90%, the results is said to be very reliable.
  The second step includes the determination of predictive factors of reliability classes. This is mandatory to identify the reliability classes. This step is the main difference between accuracy and reliability. For example, a diagnostic test having a diagnostic accuracy of 90% means that correct classification is obtained in 90% of patients by the test. The test is inaccurate or quite (100%) unreliable in 10% of the patients of the whole population. The reliability evaluation may determine that in a subject subgroup (for example 2% of patients), the accuracy rate might be 30% (i.e. higher than the inaccuracy rate in the whole population), that is an unreliable result. This unreliable result is diagnosed by one or some significant reliability predictors such as high body weight and/or a discordant marker compared to other markers (e.g. the first one is highly abnormal whereas all other markers are normal or weakly abnormal).

In one embodiment, a test is considered sufficiently reliable for diagnosis when its accuracy is of more than 50%, preferably more than 60, 70, 75, 80, 85, 90 or 95%. Accordingly, the probability of error of diagnosis considered as higher than tolerated for diagnosis is of 50%, 40%, 30%, 20%, 15%, 10% or 5%. In other words, a test is considered sufficiently reliable when the percentage of misdiagnosed subjects is less than 50%, preferably less than 40, 30, 20, 15, 10 or 5%.

According to an embodiment, the method of the invention comprises:

a. collecting a diagnostic index, called Initial Index, preferably a score, more preferably a score selected from blood tests comprising ELF, FibroSpect™, APRI, FIB-4, Hepascore, Fibrotest™, or a score from the FibroMeter family, such as for example FibroMeter™ and CirrhoMeter™ or CombiMeter™; or a test derived from the FibroMeter Family, where urea was deleted from the markers; or another diagnostic test; said index involving the mathematical combination of at least two data, preferably of at least two biomarkers, clinical markers and/or data resulting from physical method; said index being referred to as Initial Index, b. analyzing the reliability of each data by positioning the Index in a reliability class of the reliability classification based on the data obtained in a reference population;

According to this embodiment, the reliability of the Explained Data is determined by positioning said data in a reliability class of a reliability classification. In one embodiment, said reliability classification gives, for each set of data (i.e. for each combination of explained data and explanatory data), the reliability of the explained data. In one embodiment, said reliability classification was established based on the data obtained in a reference population. In an embodiment, the reliability of an Initial Index is determined by positioning said Index in a reliability class of a reliability classification including a two-entry table of Explained Data and Explanatory Data (predictors), established on the basis of a population of reference, wherein the reading of the position of the Index in the table gives the reliability of the Index with consideration to the Explanatory Data. In one embodiment, the different tests which are performed are preferably independent predictors of well classified patients. In one embodiment, the independent predictors of well classified patients by the explained data have been determined by multivariate analysis, such as, for example, by binary logistic regression.

In one embodiment, the reliability of a test is determined based on comparison of the patient result (explained data) with reliability classes, wherein reliability classes are part of a classification based on the reliability level of the test results (explained data) determined in a reference database.

In one embodiment, in this reference database, the independent predictors of well classified patients have been determined by multivariate analysis (e.g. binary logistic regression or RLB) wherein the dependent variable is the well classified patients by the diagnostic test and the independent variables are all the composite variables included in the test (intrinsic data) and available variables provided by demographic data and composite variables included in other available tests (extrinsic data). The RLB provides a score including several variables or a segmented classification. Both result in reliability classification:

The score is plotted against the rate of well classified patients and classes are determined by threshold chosen by the expert on this graph (see Examples in FIG. 3).

The segmented classification is determined by the segmentation of variables according to relationship between independent variables. The threshold can be determined by a graph plotting both variables or by classical indices like Youden index. This classification is preferably obtained when there is a significant interaction between two independent variables.

A mixed model including reliability classes determined by RLB and reliability classes provided by single variable(s) (such as, for example, inconsistent variables as defined hereinabove) can occur.

Finally, the patient result (explained data) is compared with these reliability classes and the ensuing reliability level is fixed for this patient with this test.

In one embodiment, the explained data is a diagnostic test result or an index, preferably a score, and the predictors tested to define if they are independent predictors are:

the data mathematically combined to calculate the index (intrinsic data), and explanatory data as hereinabove described (extrinsic data), and/or extrinsic data available with the diagnostic test.

An example of an intrinsic variable of a test is the dispersion index (DI), as herein above described.

Examples of reliability predictors include, but are not limited to variables included in or derived from non-invasive tests, as stated below, preferably FibroMeter, InflaMeter and Fibroscan, and more preferably urea, ALT, AST, Dispersion Index, score of CirrhoMeter$^{2G}$, score of FibroMeter$^{2G}$, Fibroscan™ classes, FibroMeter™ classes, CirrhoMeter™ classes, Fibroscan™ median, IQR, IQR/M, platelets, A2M and t=ratio urea/Fibroscan.

Examples of reliability predictors for FibroMeter$^{2G}$ and for CombiMeter™ are shown in Example 6.

Event Alert

In one embodiment, an Event Alert is issued when the explained data is non-reliable.

Triggered Response

In one embodiment, if an Event Alert is issued on the explained data, the explanatory data are considered, each in turn, as the explained data, and their reliability is checked as hereinabove described.

In one exemplary embodiment, a FibroMeter™ and a Fibroscan™ are carried out with FibroMeter™ result considered as the explained data in a first step. If an Event Alert is issued on FibroMeter™, Fibroscan™ result will be considered in a second step as the explained data, with FibroMeter™ result as explanatory data, and the reliability of Fibroscan™ will be checked.

In one embodiment of the invention, if only one test is reliable, its result is considered as the Final Data. In another embodiment of the invention, if several tests are reliable, the most reliable one is considered as given the Final Data. In another embodiment of the invention, if several tests are reliable, their combination is considered as given the Final Data. For example, in one embodiment, if Fibroscan™ and FibroMeter™ or CirrhoMeter™ are reliable, the corresponding CombiMeter™ is considered as given the Final Data.

In one embodiment, the Final Data may thus be finally used for assessing the presence and/or the severity of a liver disease in the subject. In one embodiment, said assessment includes the classification of the subject in a class of a fibrosis stage classification, i.e. a class of a classification wherein each class is associated with a fibrosis stage, such as, for example, one or more Metavir F stage(s).

In one embodiment, the method of the invention comprises releasing a comment. In one embodiment, said comment comprises indicating which one of the data has been considered as the most reliable one. In one embodiment, said comment comprises a warning message, wherein the more there are data which have been considered as non-reliable, the more the result must be considered carefully.

An example of a method of the invention comprising carrying out a FibroMeter™ and a Fibroscan™ is shown in Example 5, and the establishment of a reliability classification is shown in Example 7.

In one embodiment, the method of the invention provides an improvement in diagnostic precision through predictive values. In one embodiment, thresholds of 100% predictive values for the main diagnostic target are fixed with several diagnostic tests previously obtained in a reference database. In one embodiment, if the patient result is equal or superior to the threshold corresponding to the 100% positive predictive value, the diagnostic target is affirmed. In another embodiment, if the patient result is equal or superior to the threshold corresponding to the 100% negative predictive value, the diagnostic target is excluded.

The present invention also relates to an expert system implementing the method of the invention.

The present invention also relates to a software for implementing the method of the invention.

In one embodiment, the expert system is a software, wherein:
a. the software is fed with input data (levels of biomarkers, physical data, clinical data, scores, etc.),
b. the software implements for an individual subject, on the basis of input data (levels of biomarkers, physical data, clinical data, scores etc. . . . ), various tests using various strategies,
b. the software checks confidence of input data of each test,
c. the software analyzes the reliability of each test performed in step a,
d. the software outputs a final test corresponding to the most reliable test for this individual, and optionally a comment on the reliability of the final test.

In another embodiment, the expert system is a software, wherein:
a. the software is fed with input test (physical data, scores etc), called Explained Data,
b. the software analyses the reliability of the Explained Data using Explanatory Data,
d. the software outputs a final test corresponding to the most reliable test for this individual, optionally together with a comment on the reliability of the final test.

EXAMPLES

The present invention is further illustrated by the following examples.

Example 1

Composition of FM Family

| | | | | Variables | | | | | | | | | | | | |
|---|---|---|---|---|---|---|---|---|---|---|---|---|---|---|---|---|
| Cause | Age | Sex | Weigth | A2M | HA | PI | PLT | AST | Urea | GGT | Bili | ALT | Fer | Glu | FS | N$^a$ | Ref |
| Virus | | | | | | | | | | | | | | | | | |
| FM V 1G | x | | | x | x | x | x | x | x | | | | | | | 7 | 1 |
| FM V 2G | x | x | | x | x | x | x | x | x | | | | | | | 8 | 2 |
| CM V 2G | x | x | | x | x | x | x | x | x | | | | | | | 8 | 3 |
| FM V 3G$^b$ | x | x | | x | x | | x | x | | x | | | | | | 8 | 4 |
| CM V 3G$^b$ | x | x | | x | x | | x | x | | x | | | | | | 8 | 4 |

-continued

| | | | | | | | Variables | | | | | | | | | |
|---|---|---|---|---|---|---|---|---|---|---|---|---|---|---|---|---|
| Cause | Age | Sex | Weigth | A2M | HA | PI | PLT | AST | Urea | GGT | Bili | ALT | Fer | Glu | FS | N[a] | Ref |
| Alcohol | | | | | | | | | | | | | | | | |
| FM A 1G | x | | | | x | x | x | | | | | | | | | 4 | 2 |
| FM A 2G | | | | | x | x | x | | | | | | | | | 3 | — |
| NAFLD (steatosis) | | | | | | | | | | | | | | | | |
| FM S | x | | x | | | | | x | x | | | x | x | x | | 7 | 5 |

FM: FibroMeter,
CM: CirrhoMeter,
A2M: alpha-2 macroglobulin,
HA: hyaluronic acid,
PI: prothrombin index,
PLT: platelets,
Bili: bilirubin,
Fer: ferritin,
Glu: glucose,
FS: Fibroscan
[a]Number of variables
[b]HA may be replaced by GGT In an embodiment, the Explained Data is test derived from the Fibrometer Family, where urea was deleted from the markers

REFERENCES

1. Calèes P, Oberti F, Michalak S, Hubert-Fouchard I, Rousselet M C, Konate A, Gallois Y, et al. A novel panel of blood markers to assess the degree of liver fibrosis. Hepatology 2005; 42:1373-1381.
2. Leroy V, Hilleret M N, Sturm N, Trocme C, Renversez J C, Faure P, Morel F, et al. Prospective comparison of six non-invasive scores for the diagnosis of liver fibrosis in chronic hepatitis C. J Hepatol 2007; 46: 775-782.
3. Boursier J, Bacq Y, Halfon P, Leroy V, de Ledinghen V, de Muret A, Bourlière M, et al. Improved diagnostic accuracy of blood tests for severe fibrosis and cirrhosis in chronic hepatitis C. Eur J Gastroenterol Hepatol 2009; 21:28-38.
4. Calès P, Boursier J, Bertrais S, Oberti F, Gallois Y, Hubert IF, Dib N, Zarski J P, Rousselet M C; multicentric groups (SNIFF 14 & 17, ANRS HC EP 23 Fibrostar). Optimization and robustness of blood tests for liver fibrosis and cirrhosis. Clin Biochem. 2010; 43; 1315-1322.
5. Calès P, Lainé F, Boursier J, Deugnier Y, Moal V, Oberti F, Hunault G, et al. Comparison of blood tests for liver fibrosis specific or not to NAFLD. J Hepatol 2009; 50:165-173.

Example 2

Dispersion Index of FibroMeter Modified by the Method of the Invention

Figure 1:
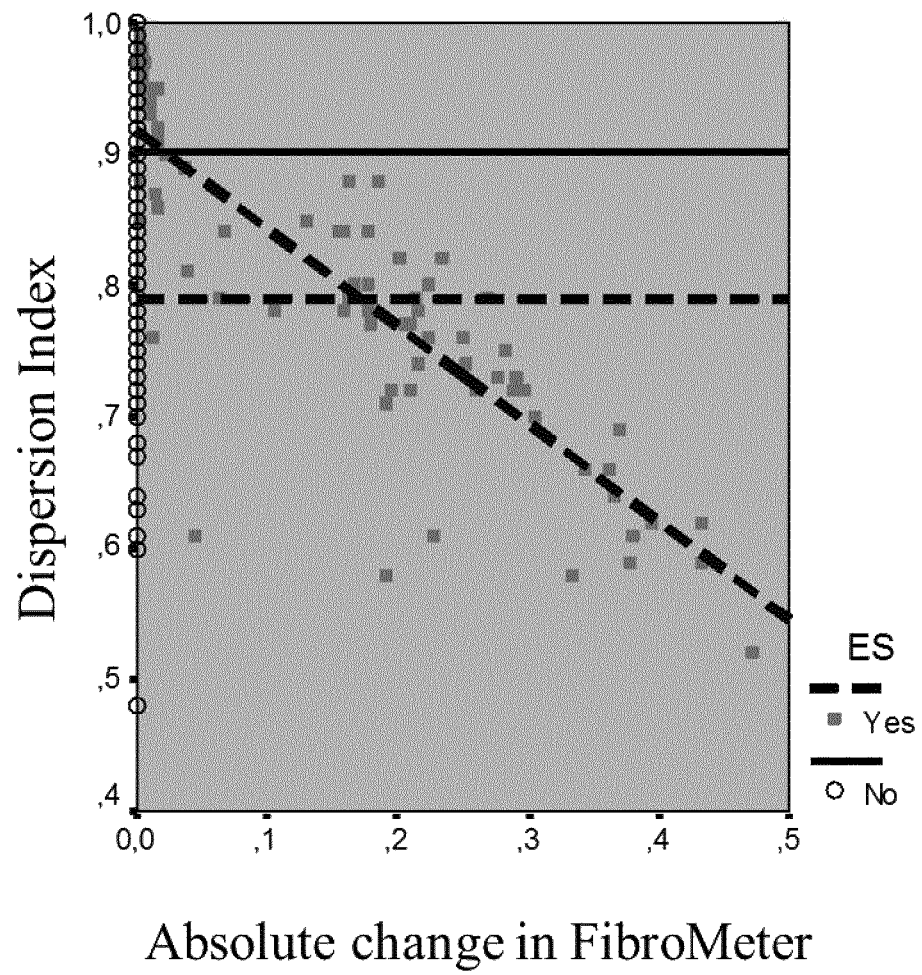
FIG. 1 is a graph showing that the dispersion index of initial FibroMeter™ is well correlated (oblique dashed line) with the difference between initial (no ES—expert System—) and final (yes ES) FibroMeter™ modified according to the method of the invention. The horizontal lines denote the means. Population of 825 patients with chronic hepatitis C.
Figure 2:
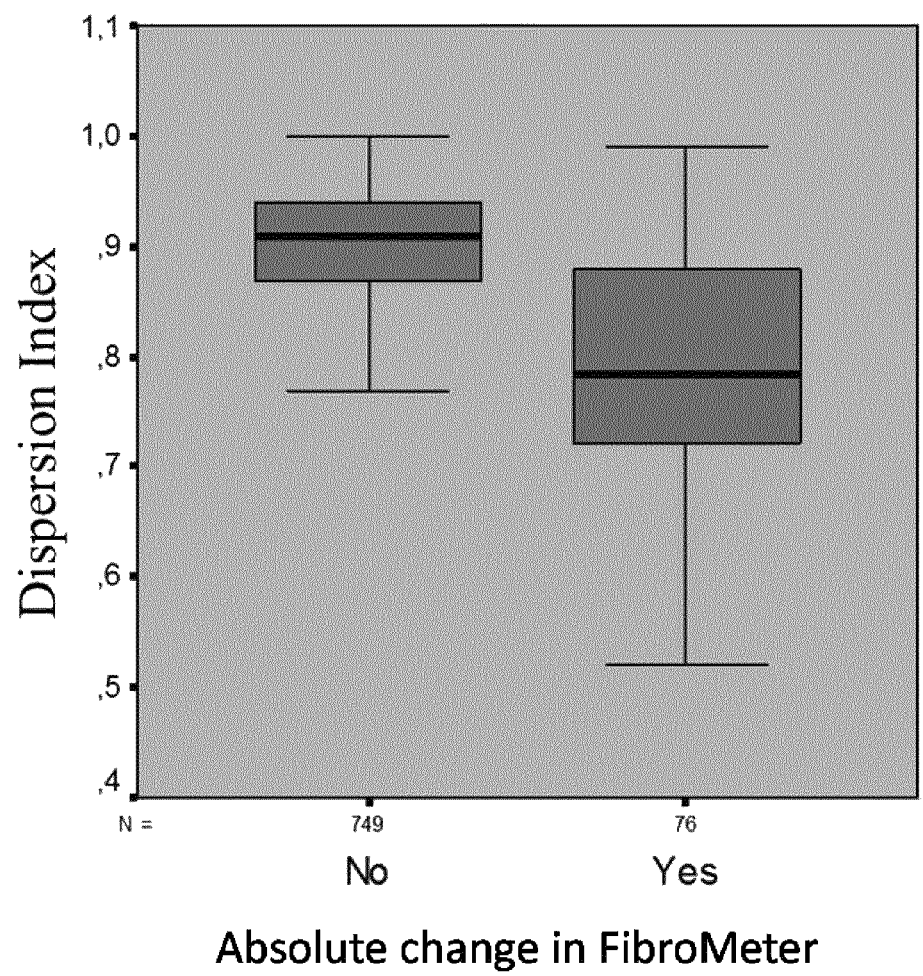
FIG. 2 is a graph showing that the dispersion index is significantly different between values of FibroMeters not modified (No) or modified (Yes) (in 9.2% of cases on right box) by the method of the invention. Box plots: median, interquartiles and extremes. Population of 825 patients with chronic hepatitis C.

FIG. 1 and FIG. 2 show that the method of the invention leads to an improvement in the determination of the reliability of FibroMeter™, as denoted by the analysis of the dispersion index of FibroMeter™ before (i.e. Initial score) and after (i.e. Final score) the method of the invention is carried out. Patients behind the dispersion thresholds (Y axis) have a decreased reliability. Note that in this population of 825 patients most patient symbols are superimposed in the left superior corner.

FIG. 1 shows that when the dispersion index (DI) is high, the Expert System of the invention does not give an Alternative or Estimated Index, and Final Index is Initial Index. In other words, the DI is a good predictor of reliability of a non-invasive method for assessing presence and/or severity of a liver disease. FIG. 1 shows the efficacy of the method of the invention.

Example 3

Abnormal Data, Consistency and Inconsistency Ranges for FibroMeter™ (Table 1)

TABLE 1

| | | PLT (G/L) | AST (IU/L) | Urea (mmol/L) | HA (µg/L) | PI (%) | A2M (mg/dL) | Age (year) |
|---|---|---|---|---|---|---|---|---|
| Abnormal data | | 5-20 | 500-20000 | 0-1 | 2000-3000 | 5-20 | 500-1000 | 99-120 |
| False positive | Red | 20-110 | 110-500 | <1-1.2 | 73-2000 | 20-79 | 402-500 | 82-99 |
| inconsistency range | Yellow | 110-170 | 68-110 | 1.2-2.9 | 51-73 | 79-88 | 311-402 | 66-82 |
| Consistency range | | 170-308 | 6-68 | 2.9-6.7 | 24-51 | 88-109 | 105-311 | 29-66 |
| False positive | Green | 308-390 | N/A | 6.7-8.8 | 11-24 | 109-121 | 100-105 | 8-29 |

TABLE 1-continued

|  |  | PLT (G/L) | AST (IU/L) | Urea (mmol/L) | HA (µg/L) | PI (%) | A2M (mg/dL) | Age (year) |
|---|---|---|---|---|---|---|---|---|
| inconsistency range | Blue | 390-800 | N/A | 8.8-15 | N/A | 121-150 | N/A | 6-8 |
| Abnormal data | | 800-2000 | 0-6 | 15-70 | 0-11 | 150 | 10-100 | 0-6 |

A2M: alpha-2 macroglobulin,
HA: hyaluronic acid,
PI: prothrombin index,
PLT: platelets,
AST: aspartate aminotransferase Example 4

Examples of Preliminary Analysis Rules of Event Alerts Issued wherein a FibroMeter™ is Carried Out Here are presented some preliminary analysis rules of the Inconsistent Data Event Alerts issued when a FibroMeter™ is carried out. In this example, 4 types of Inconsistent Data Alerts are issued: Red, Yellow, Green and Blue, according to the Table of Example 1.

Suppression of Event Alerts if AST is the only one Red Alert and if there is no Yellow Alert, the Red Alert is suppressed.

if there are one Red Alert and one Yellow Alert, both may be suppressed, except when one of these Event Alerts was issued by the data AGE. In this situation, only the Event Alert issued by AGE is suppressed.

if there is more than one Red or two Yellow Alerts, these alerts are suppressed.

if an Event Alert is issued by the data AGE, said Event Alert is suppressed.

Prioritization of Event Alerts

If several Inconsistent Data Alerts subsist after suppression of Event Alerts as hereinabove described, the prioritization of said Event Alerts (i.e. the selection of the main alert) is carried out as follows (Table 2—all situations are not represented):

TABLE 2

| Number of Event Alerts | Type and number of Event Alert | | | | Main Alert |
|---|---|---|---|---|---|
| | Red | Yellow | Blue | Green | |
| 2 | 1 | | 1 | | Red |
| | | 1 | 1 | | Blue |

TABLE 2-continued

| Number of Event Alerts | Type and number of Event Alert | | | | Main Alert |
|---|---|---|---|---|---|
| | Red | Yellow | Blue | Green | |
| | 1 | | | 1 | Red |
| | 1 | 1 | | | Red |
| 3 | 1 | 1 | 1 | | Red |
| | 1 | | 1 | 1 | Red |
| | 1 | 1 | | 1 | Red |
| 4 | 1 | 1 | 1 | 1 | Red |

If several Event Alerts of the same type (such as, for example, two Red Alerts or two Green Alerts) are issued, the main one will be the one issued by the data being the furthest from its mean value.

Example 5

Examples of Reliability Classifications

In the tables below, the "reliability" corresponds to the percentage of correctly classified patients in a given class. The "% of patients" corresponds to the percentage of patients of the reference population classified in this given class. Any reference to a "F" class is made with reference to estimated Metavir F stages. The reference population comprises about 600 patients.

Reliability of Fibroscan (Table 3)

The explained data is the classification based on Fibroscan, whereas the explanatory data are score from CirrhoMeter$^{2G}$ (CM$^{2G}$), score from FibroMeter$^{2G}$ (FM$^{2G}$), AST, and ALT.

TABLE 3

| Explained Data (Fibroscan classification) | Explanatory data | | | | Reliability | % of patients |
|---|---|---|---|---|---|---|
| | CM$^{2G}$ | FM$^{2G}$ | AST | ALT | | |
| ≤F2 | ≤0.13 | | <26 | | 81 | 5.9 |
| | | | ≥26 | | 92.1 | 60.1 |
| | >0.13 | | | <70 | 87.5 | 3.6 |
| | | | | ≥70 | 68.6 | 5.2 |
| ≥F3 | | <0.40 | | | 20 | 2.2 |
| | | 0.40 ≤ FM$^{2G}$ < 0.71 | | | 69.2 | 3.9 |
| | | ≥0.71 | | | 95.3 | 19.1 |

In conclusion, as shown in Table 3, more than 92% patients classified as ≤F2 after carrying out a Fibroscan, and having a score of CirrhoMeter$^{2G}$ inferior or equal to 0.13 and ASAT quantification superior or equal to 26 IU/L are well-classified. This situation concerns about 60% of patients.

On the contrary, about 80% of patients classified in ≥F3 after a Fibroscan and having a FibroMeter$^{2G}$ score inferior to 0.40 are misdiagnosed. Accordingly, Fibroscan is not a reliable test for these patients, which represent about 2% of the patients.

Reliability of FibroMeter$^{2G}$ (Table 4)

The explained data is the classification based on FibroMeter$^{2G}$ (FM$^{2G}$ classes), whereas the explanatory data are classification from Fibroscan (FS classes), score from FibroMeter$^{2G}$ (FM$^{2G}$), ratio urea/score resulting from a Fibroscan (urea/FS), IQR (Inter Quartile Range from Fibroscan) and platelets.

TABLE 4

| Explained Data | Explanatory Data | | | | | % of |
|---|---|---|---|---|---|---|
| (FM$^{2G}$ classes) | FS classes | IQR | Platelets | FM$^{2G}$ | urea/FS | Reli- ability | pa- tients |
| ≤F2 | <2 | ≤1.0 | | | | 91.7 | 23.4 |
| | | >1.0 | | | | 84.8 | 9.9 |
| | | | | | | 76.9 | 3.9 |
| | 2 | | >285 | | | 95 | 18.0 |
| | >2 | | | ≤0.43 | | 23.5 | 2.5 |
| | | | | | | 72 | 3.7 |
| ≥F3 | | | | | <1.015 | 92.1 | 34.3 |
| | | | | | ≥1.015 | 78.6 | 4.2 |

In conclusion, as shown in Table 4, more than 91% patients classified as ≤F2 after carrying out a FibroMeter$^{2G}$, and classified as F<2 after a Fibroscan with an IQR inferior or equal to 1.0 are well-classified. FibroMeter$^{2G}$ is thus a reliable test for these patients, representing about 23% of the population. The same conclusion may be made for patients classified as ≥F3 after carrying out a FibroMeter$^{2G}$, and having a ratio urea/FS inferior to 1.015.

On the contrary, about 78% of patients classified in ≥F3 after a FibroMeter$^{2G}$ and having a FibroMeter$^{2G}$ score inferior to 0.43 are misdiagnosed. Accordingly, FibroMeter$^{2G}$ is not a reliable test for these patients, which represent about 2.5% of the population.

Example 6

Examples of Reliability Predictors

Reliability Predictors for FibroMeter$^{2G}$ (Table 5)

Examples of reliability predictors for FibroMeter$^{2G}$ are shown in the Table 5 below. Population of 597 patients with chronic hepatitis C. FS: Fibroscan, FM: FibroMeter.

TABLE 5

| Segmentation | Reliability predictors | Notes |
|---|---|---|
| All patients | FS classes, ALT, IQR/M | Significant interaction between FS classes and ALT justifying the next step: |
| 1. FS classes < 3 | FM classes, FS classes, AST, IQR | Significant interaction with AST justifying the next step: |
| AST > 185 | | 100% misclassified patients |
| AST < 185 | FM classes, FS classes, IQR | These 3 data are included in a Score #1 |
| 2. FS classes ≥ 3 | FM classes, ALT, A2M | These 3 data are included in a Score #2 |
| ALT > 430 | | 100% misclassified patients |

The method of the invention for determining the reliability of FibroMeter$^{2G}$ for a patient includes, in this example, two steps:

1/apply variables threshold (for AST or ALT) that determine 100% misclassified patients; and
2/then apply the multivariate score in the other patients.

Figure 3:
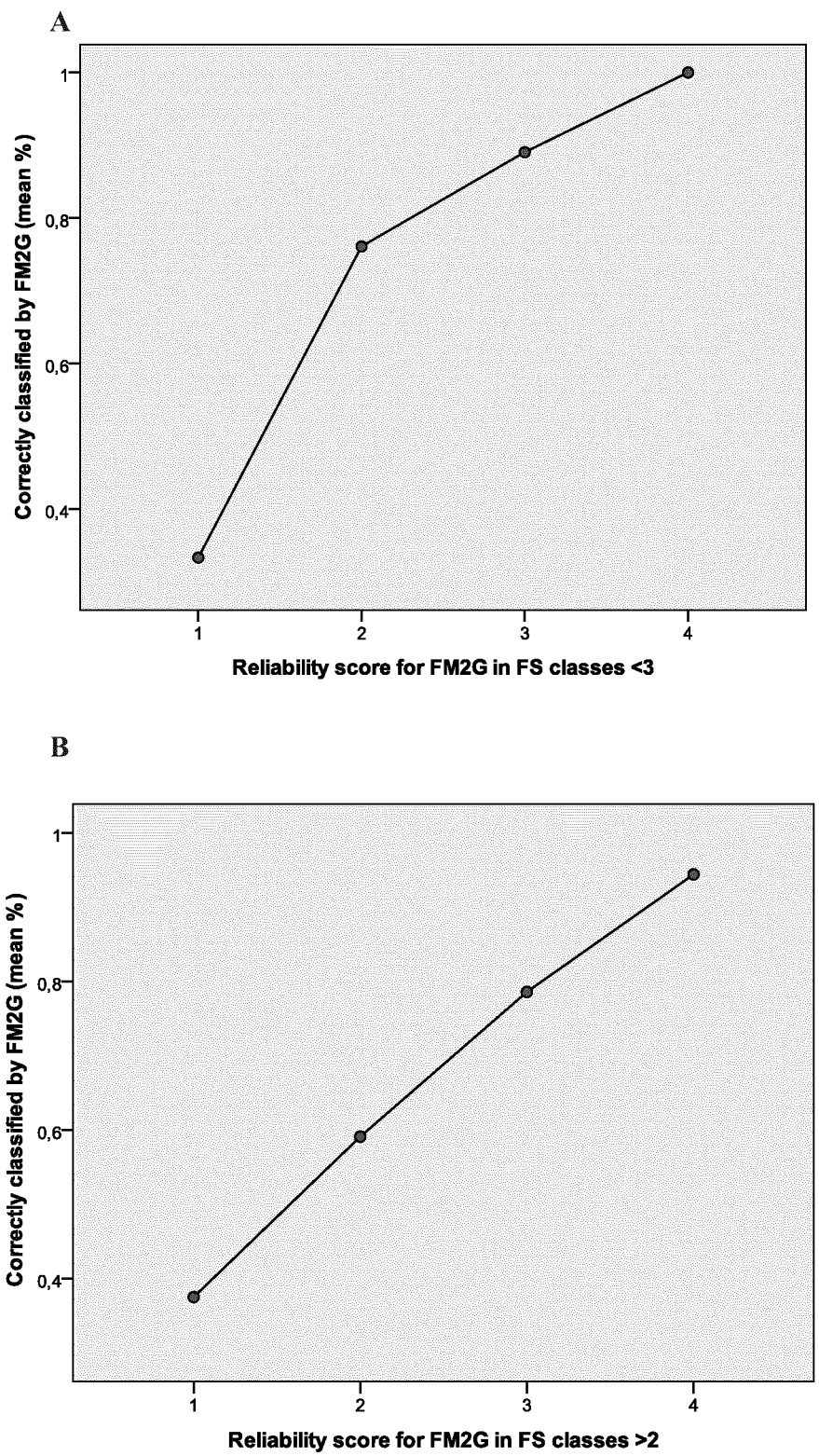
FIG. 3 is a combination of graphs showing the percentage of correctly classified patients using FibroMeter$^{2G}$ (FM2G) according to the reliability score for FibroMeter$^{2G}$ in Fibroscan™ classes <3 (A) or >2 (B).
Figure 4:
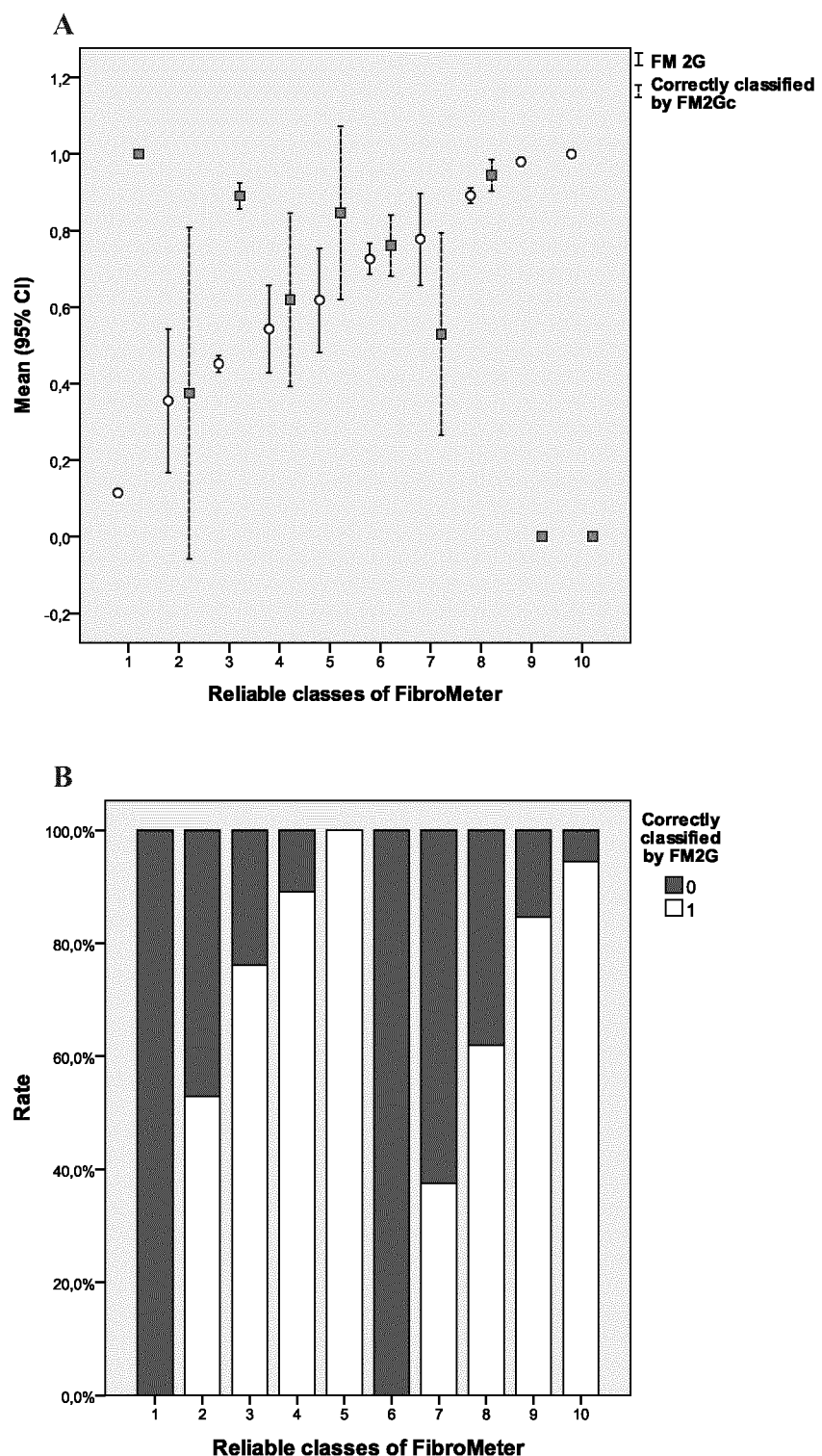
FIG. 4 is a combination of graphs showing the relevance of reliability classes. (4A) shows the relationship between FibroMeter score (continuous lines) and accuracy (dashed lines) on Y axis as a function of 10 reliability classes for FibroMeter on X axis. Reliability classes on X axis are ranked according to increasing FibroMeter score. (4B) shows the accuracy of FibroMeter score as a function of 10 reliability classes for FibroMeter. In the figure, the 5 first classes are those of FS classes <3 ($p<0.001$) and the 5 last are those of FS classes ≥3 ($p<0.001$).

FIG. 3 and FIG. 4 show the relevance of reliability classes.

For patients classified in Fibroscan (FS) fibrosis classes <3, the efficacy of predictive score including 3 predictors (score #1) is shown in FIG. 3A where the score distinguishes 4 reliability classes (reliability scores) on X axis (p<0.001 by ANOVA).

For patients classified in FS classes >2, the efficacy of predictive score including 3 predictors (score #2) is shown in FIG. 3B where the score distinguishes 4 reliability classes (reliability scores) on X axis (p<0.001 by ANOVA).

In FIG. 4, the 5 first classes are those of FS classes <3 (p<0.001) and the 5 last are those of FS classes ≥3 (p<0.001). FIG. 4A shows the relationship between FibroMeter score (continuous lines) and accuracy (dashed lines) on Y axis as a function of 10 reliability classes for FibroMeter on X axis. Reliability classes on X axis are ranked according to increasing FibroMeter score. FIG. 4B shows the accuracy of FibroMeter score as a function of 10 reliability classes for FibroMeter Reliability Predictors for CombiMeter™ (Table 6)

Examples of reliability predictors for CombiMeter™ are shown in Table 6 below. They include Fibroscan classes, Fibroscan median, Urea, score of FibroMeter$^{2G}$ (FM2G), CirrhoMeter$^{2G}$ classes (CM2G classes) and AST.

TABLE 6

| Reliability predictors | | | |
|---|---|---|---|
| 1$^{st}$ rank Fibroscan classes | 2$^{nd}$ rank | Reliability classes | Accuracy |
| ≤2 | Fibroscan median | | |
| | ≥10.5 | 1a | Suboptimal reliability |
| =3 | <10.5 | 1b | Very reliable |
| | Urea | | |
| | >8 | 2a | Unreliable |
| | ≤8 | 2b | Suboptimal reliability |
| =3.5 | FM2G | | |
| | <0.3 | 3a | Fairly reliable |
| | ≥0.3 | 3b | Very reliable |
| =4 | CM2G classes ≤2 | 4a | Unreliable |
| | AST >400 | 4b | Unreliable |
| | Others | 4c | Reliable |

Example 7

Classification of LSE accuracy

Patients and Methods

Patients

Two populations with liver biopsy and LSE were included in the present study. LSE stands for Liver stiffness evaluation (LSE) and corresponds to all the measurements recorded during an examination with the Fibroscan device. The first population was composed of patients with chronic liver disease recruited in 3 French centers between 2004 and 2009 (Angers: n=383; Bordeaux: n=309; and Grenoble: n=142). Patients included in the Angers and Bordeaux centers had various causes of chronic liver diseases whereas those from Grenoble had CHC. The second population was that of the multicenter ANRS/HC/EP23 Fibrostar study promoted by the French National Agency for Research in AIDS and Hepatitis (Zarski et al, J Hepatol 2012; 56:55-62). The patients included in both populations were identified and ultimately grouped as a single observation for statistical analyses. All patients gave their written informed consent. The study protocol conformed to the ethical guidelines of the current Declaration of Helsinki and received approval from the local ethics committees.

Histological Assessment

Liver fibrosis was evaluated according to Metavir fibrosis ($F_M$) staging. Significant fibrosis was defined as Metavir $F_M \geq 2$, severe fibrosis as Metavir $F_M \geq 3$, and cirrhosis as Metavir $F_M 4$. In the first population, histological evaluations were performed in each center by blinded senior pathologists specialized in hepatology. In the Fibrostar study, histological lesions were centrally evaluated by two senior experts with a consensus reading in cases of discordance. Fibrosis staging was considered as reliable when liver specimen length was $\geq 15$ mm and/or portal tract number $\geq 8$.

Liver Stiffness Evaluation

Examination conditions—LSE by Fibroscan (Echosens, Paris, France) was performed with the M probe (wherein M probe is a standard probe while they are specific probes for obese patients or children) and by an experienced observer (>50 examinations before the study), blinded for patient data. A time interval of $\leq 3$ months between liver biopsy and LSE was considered acceptable for the purposes of the study. Examination conditions were those recommended by the manufacturer, with the objective of obtaining at least 10 valid measurements. A LSE measurement corresponds to a single measurement of liver stiffness, i.e., after pushing the button of the Fibroscan probe. Measurement validity was determined by an internal process defined by the Fibroscan manufacturer. Validity is evaluated for each LSE measurement: the liver stiffness is displayed on the screen when the measurement is considered as "valid", and not displayed if it is considered as "invalid". Results were expressed as the median and the IQR (kilopascals) of all valid measurements: LSE median (kPa) corresponds to the median of all the valid measurements performed during LSE; and LSE interquartile range (IQR) (kPa) corresponds to the interval around the LSE median containing 50% of the valid measurements between the 25$^{th}$ and 75$^{th}$ percentiles.

According to the usual definition, LSE was considered as reliable when it included $\geq 10$ valid measurements with a success rate $\geq 60\%$ and IQR/M$\leq 0.30$, wherein the success rate (%) is calculated as the ratio of the number of valid measurements over the total number of measurements performed during LSE.

Interpretation of LSE result—LSE median was interpreted according to the diagnostic cut-offs published in previous studies. As chronic hepatitis C (CHC) was the main cause of liver disease in our study population (68%), we tested the cut-offs published by Castera et al. (Castera et al, Gastroenterology, 2005; 128:343-50): $\geq 7.1$ kPa for $F_M \geq 2$ and $\geq 12.5$ kPa for $F_M 4$, those by Ziol et al. (Hepatology 2005; 41:48-54): $\geq 8.8$ kPa for $F_M \geq 2$ and $\geq 14.6$ kPa for $F_M 4$, and those specifically calculated for CHC in the meta-analysis of Stebbing et al (Journal of Clinical Gastroenterology 2010; 44:214-9): $\geq 8.5$ kPa for $F_M \geq 2$ and $\geq 16.2$ kPa for $F_M 4$. As there were various causes of chronic liver disease in our study population, we also tested the cut-off published in the meta-analysis of Friedrich-Rust et al. (Gastroenterology 2008; 134:960-74): $\geq 7.7$ kPa for $F_M \geq 2$ and $\geq 13.1$ kPa for $F_M 4$. By using the diagnostic cut-offs, LSE median was categorized into estimated $F_{FS}$ stages according to the most probable Metavir F stage(s). This approach provided the following LSE classification: LSE result <cut-off for $F_M \geq 2$: $F_{FS} 0/1$; $\geq$cut-off for $F_M \geq 2$ and <cut-off for $F_M 4$: $F_{FS} 2/3$; $\geq$cut-off for $F_M 4$: $F_{FS} 4$.

Statistical Analysis

Because distribution was skewed for most quantitative variables, they were expressed as median with 1$^{st}$ and 3$^{rd}$ quartiles into brackets. Diagnostic accuracy was mainly expressed as AUROC (for binary diagnoses of significant fibrosis, severe fibrosis, or cirrhosis) or the rate of well-classified patients by the LSE classification. AUROCs were compared according to Delong et al. for paired groups (Biometrics 1988; 44:837-45), and Hanley et al. for unpaired groups (Radiology 1982; 143:29-36).

To identify the factors influencing LSE accuracy, we determined the variables independently associated with the following diagnostic target: significant fibrosis, severe fibrosis, or cirrhosis by stepwise forward binary logistic regression. Indeed, by definition, each variable selected by a multivariate analysis is an independent predictor of the diagnostic target studied. In other words, when selected with LSE median, an independent predictor influences the outcome (diagnostic target) for each fixed level of liver stiffness. Consequently, the multivariate analyses allowed for the identification of the predictor influencing LSE accuracy regarding fibrosis staging. In the present study, the dependent variable—LSE median—was tested with the following independent variables: age, sex, body mass index, cause of chronic liver disease (CHC versus other), $\geq 10$ LSE valid measurements, LSE success rate, IQR/M (wherein IQR/M corresponds to the ratio LSE IQR/LSE median), and biopsy length as a putative confounding variable. Statistical analyses were performed using SPSS version 18.0 software (IBM, Armonk, N.Y., USA) and SAS 9.1 (SAS Institute Inc., Cary, N.C., USA).

Results

Patients

The main characteristics of the 1165 patients included in the study are presented in Table 7. The cause of chronic liver disease was CHC in 68.5% of patients, hepatitis B mono-infection: 5.7%, alcohol: 12.4%, non-alcoholic fatty liver disease: 3.3%, and other: 10.1%. Overweight status (body mass index $\geq 25.0$ kg/m$^2$) was present in 44.0% of patients. Liver biopsies were considered as reliable in 92.0% of the cases. The prevalence for significant fibrosis, severe fibrosis, and cirrhosis was respectively 63.3%, 38.9%, and 21.0%.

TABLE 7

| | Cause of liver disease | | | |
|---|---|---|---|---|
| | All | CHC | Other | p $^a$ |
| Patients (n) | 1165 | 798 | 367 | — |
| Age (years) | 51.1 (43.9-60.5) | 50.1 (43.9-59.7) | 54.2 (43.9-63.3) | 0.084 |
| Male (%) | 65.2 | 62.9 | 70.0 | 0.018 |
| Body mass index (kg/m$^2$) | 24.5 (22.2-27.6) | 24.2 (22.1-26.7) | 25.1 (22.5-29.4) | <10$^{-3}$ |

TABLE 7-continued

| | Cause of liver disease | | | |
|---|---|---|---|---|
| | All | CHC | Other | p [a] |
| Body mass index ≥ 25 kg/m² (%) | 44.0 | 40.1 | 50.9 | $10^{-3}$ |
| Metavir $F_M$ stage (%): | | | | $<10^{-3}$ |
| 0 | 5.6 | 3.5 | 10.3 | |
| 1 | 31.0 | 37.1 | 17.6 | |
| 2 | 24.5 | 27.4 | 17.9 | |
| 3 | 17.9 | 17.5 | 18.7 | |
| 4 | 21.0 | 14.5 | 35.5 | |
| Biopsy length (mm) | 25 (18-30) | 24 (18-30) | 25 (17-32) | 0.093 |
| Reliable biopsy (%) | 92.0 | 93.8 | 88.0 | $10^{-3}$ |
| LSE median (kPa) | 8.1 (5.8-14.0) | 7.8 (5.6-11.1) | 11.0 (6.6-25.1) | $<10^{-3}$ |
| Valid measurements (n) | 10 (10-10) | 10 (10-10) | 10 (10-10) | 0.227 |
| ≥10 LSE valid measurements (%) | 92.8 | 93.3 | 91.6 | 0.291 |
| LSE success rate (%) | 100 (83-100) | 100 (83-100) | 91 (77-100) | $10^{-3}$ |
| LSE success rate ≥ 60% (%) | 89.8 | 91.9 | 85.1 | $<10^{-3}$ |
| IQR/M | 0.17 (0.12-0.25) | 0.17 (0.12-0.24) | 0.18 (0.11-0.25) | 0.211 |
| IQR/M ≤ 0.30 (%) | 85.5 | 86.1 | 84.3 | 0.416 |
| Reliable LSE (%) [b] | 75.7 | 77.6 | 71.6 | 0.027 |

CHC: chronic hepatitis C mono-infection,
IQR/M: LSE interquartile range/LSE median;
[a] Between CHC and other causes of liver disease;
[b] According to the usual definition for LSE reliability (≥10 valid measurements and ≥60% success rate and IQR/M ≤ 0.30)

LSE Accuracy

The AUROCs (±SD) of LSE for the diagnosis of significant fibrosis, severe fibrosis, and cirrhosis were respectively 0.822±0.012, 0.872±0.010, and 0.910±0.011 (Table 8).

TABLE 8

| Cause of Liver disease | Diagnostic target | Liver stiffness evaluation | | | |
|---|---|---|---|---|---|
| | | All | Reliable [a] | Unreliable | p [b] |
| All | $F_M \geq 2$ | 0.822 ± 0.012 | 0.835 ± 0.014 | 0.794 ± 0.026 | 0.165 |
| | $F_M \geq 3$ | 0.872 ± 0.010 | 0.881 ± 0.012 | 0.856 ± 0.023 | 0.344 |
| | $F_M 4$ | 0.910 ± 0.011 | 0.913 ± 0.012 | 0.906 ± 0.022 | 0.780 |
| CHC | $F_M \geq 2$ | 0.787 ± 0.016 | 0.805 ± 0.018 | 0.733 ± 0.037 | 0.080 |
| | $F_M \geq 3$ | 0.843 ± 0.015 | 0.856 ± 0.016 | 0.811 ± 0.035 | 0.242 |
| | $F_M 4$ | 0.897 ± 0.016 | 0.900 ± 0.018 | 0.918 ± 0.038 | 0.669 |
| Other | $F_M \geq 2$ | 0.883 ± 0.019 [c] | 0.888 ± 0.024 [d] | 0.889 ± 0.032 [c] | 0.980 |
| | $F_M \geq 3$ | 0.905 ± 0.016 [d] | 0.913 ± 0.018 [e] | 0.888 ± 0.034 | 0.516 |
| | $F_M 4$ | 0.908 ± 0.016 | 0.920 ± 0.018 | 0.862 ± 0.037 | 0.159 |

CHC: chronic hepatitis C mono-infection;
[a] According to the usual definition for LSE reliability (LSE with ≥10 valid measurements and ≥60% success rate and LSE interquartile range/LSE median ≤ 0.30);
[b] Between reliable and unreliable LSE;
[c] $p \leq 10^{-3}$ vs CHC patients;
[d] $p \leq 0.010$ vs CHC patients;
[e] $p \leq 0.05$ vs CHC patient AUROCs of LSE in unreliable biopsies were not significantly different than in reliable biopsies (details not shown). The rates of well-classified patients according to the various diagnostic cut-offs tested are presented in Table 9.

TABLE 9

| Diagnostic target | Diagnostic cut-off | | Cause of liver disease | | | |
|---|---|---|---|---|---|---|
| | Reference | Cut-off | All | CHC | Other | p [a] |
| $F_M \geq 2$ | Castera et al | ≥7.1 | 74.8 [b] | 71.2 [b] | 82.7 | $<10^{-3}$ |
| | Ziol et al | ≥8.8 | 70.1 | 66.0 | 79.1 | $<10^{-3}$ |
| | Stebbing et al | ≥8.5 | 70.9 | 66.4 | 80.7 [c] | $<10^{-3}$ |
| | Friedrich-Rust et al | ≥7.7 | 73.2 [d] | 69.3 [d] | 81.8 | $<10^{-3}$ |
| $F_M 4$ | Castera et al | ≥12.5 | 84.8 [d] | 86.2 [d] | 81.8 | 0.059 |
| | Ziol et al | ≥14.6 | 86.1 | 87.9 | 82.1 | 0.008 |
| | Stebbing et al | ≥16.2 | 86.8 | 88.8 | 82.4 | 0.003 |
| | Friedrich-Rust et al | ≥13.1 | 85.3 [e] | 86.8 [e] | 82.1 | 0.038 |
| LSE | Castera et al [f] | — | 62.0 [c] | 59.7 [c] | 67.0 | 0.018 |

TABLE 9-continued

| Diagnostic target | Diagnostic cut-off | | Cause of liver disease | | | |
|---|---|---|---|---|---|---|
| | Reference | Cut-off | All | CHC | Other | p[a] |
| classification | Ziol et al[g] | — | 58.8 | 56.2 | 64.5 | 0.008 |
| | Stebbing et al[h] | — | 59.8 | 57.1 | 65.6 | 0.006 |
| | Friedrich-Rust et al[i] | — | 61.2[c] | 58.6 | 67.0 | 0.007 |

CHC: chronic hepatitis C mono-infection;
[a]Between CHC and other;
[b]p < 0.05 vs other;
[c]p < 0.05 vs Ziol;
[d]p ≤ 0.05 vs Ziol or Stebbing;
[e]p ≤ 0.05 vs Stebbing;
[f]LSE classification is derived from the cut-off for significant fibrosis and the cut-off for cirrhosis as follow: <7.1 kPa: $F_{FS}0/1$, ≥7.1 kPa and <12.5 kPa: $F_{FS}2/3$, ≥12.5 kPa: $F_{FS}4$;
[g]LSE classification: <8.8 kPa: $F_{FS}0/1$, ≥8.8 kPa and <14.6 kPa: $F_{FS}2/3$, ≥14.6 kPa: $F_{FS}4$;
[h]LSE classification: <8.5 kPa: $F_{FS}0/1$, ≥8.5 kPa and <16.2 kPa: $F_{FS}2/3$, ≥16.2 kPa: $F_{FS}4$;
[i]LSE classification: <7.7 kPa: $F_{FS}0/1$, ≥7.7 kPa and <13.1 kPa: $F_{FS}2/3$, ≥13.1 kPa: $F_{FS}4$ Cut-offs published by Castera et al. provided the highest accuracy for significant fibrosis and LSE classification, and were thus used for further statistical analysis.

Usual Definition for LSE Reliability 92.8% of LSE included at least 10 valid measurements, 89.8% achieved a ≥60% success rate, and 85.5% had an IQR/M≤0.30 (Table 7). None of these conditions led to a significant increase in LSE AUROC.

75.7% of LSE fulfilled these 3 criteria; they were consequently considered as reliable according to the usual definition for LSE reliability. A single LSE measurement may be erroneous because of various conditions (probe position or inclination, respiratory movement, etc.). The reliability criteria of LSE thus correspond to the conditions required before considering LSE median as the "real" liver stiffness. In this setting, liver stiffness evaluation is usually considered as reliable when it fulfills all the following criteria: ≥10 valid measurements, ≥60% success rate, and IQR/median ratio (IQR/M) ≤0.30.

AUROCs for significant fibrosis, severe fibrosis, or cirrhosis were not significantly different between reliable and unreliable LSE (Table 8). By using Castera et al. cut-offs (≥7.1 kPa for $F_M$≥2 and ≥12.5 kPa for $F_M$4), LSE accuracy was not significantly different between reliable and unreliable LSE for the diagnosis of significant fibrosis (respectively: 75.5% vs 72.1%, p=0.255) or cirrhosis (85.8% vs 81.5%, p=0.082). Similarly, the rate of well-classified patients by the LSE classification ($F_{FS}0/1$, $F_{FS}2/3$, $F_{FS}4$) derived from Castera cut-offs was not significantly different between reliable and unreliable LSE (respectively: 63.5% vs 57.2%, p=0.064).

Independent Predictors of Fibrosis Staging

Independent predictors of significant fibrosis, severe fibrosis, or cirrhosis are detailed in Table 10.

TABLE 10

| Diagnostic target | Step | Variable | p | Odds ratio (95% CI) |
|---|---|---|---|---|
| $F_M$ ≥ 2 | 1st | LSE median | <10⁻³ | 1.323 (1.262-1.387) |
| | 2nd | Age | <10⁻³ | 1.023 (1.011-1.035) |
| | 3rd | IQR/M | 0.002 | 0.197 (0.072-0.543) |
| $F_M$ ≥ 3 | 1st | LSE median | <10⁻³ | 1.278 (1.234-1.324) |
| | 2nd | IQR/M | 10⁻³ | 0.121 (0.034-0.433) |
| | 3rd | Age | 0.007 | 1.017 (1.005-1.030) |
| $F_M$4 | 1st | LSE median | <10⁻³ | 1.201 (1.168-1.234) |
| | 2nd | Biopsy length | 0.002 | 0.965 (0.944-0.987) |
| | 3rd | IQR/M | 0.005 | 0.070 (0.011-0.442) |

Briefly, in addition to LSE median, IQR/M was the only LSE characteristic independently associated with the three diagnostic targets of fibrosis, with no significant influence of the number of LSE valid measurements, LSE success rate, or the cause of liver disease. There was no colinearity between LSE median and IQR/M (Spearman coefficient correlation=0.047, p=0.109). Independent predictors were the same when variables were introduced as dichotomous results (IQR/M≤0.30, LSE success rate ≥60%, reliable vs unreliable biopsy) in the multivariate analyses (detailed data not shown).

Classification of LSE Accuracy

We develop here a classification using the preceding independent predictors of accuracy.

IQR/M—LSE accuracy decreased when IQR/M increased and three subgroups of LSE were identified: IQR/M≤0.10 (16.6% of patients); 0.10<IQR/M≤0.30 (69.0%); IQR/M<0.30 (14.5%). LSE with IQR/M<0.10 had significantly higher accuracy than LSE with IQR/M>0.10 (Table 11).

TABLE 11

| | | AUROC | | | Diagnostic accuracy (%)[a] | | |
|---|---|---|---|---|---|---|---|
| | | | | | | | LSE |
| Diagnostic target: | | $F_M$ ≥ 2 | $F_M$ ≥ 3 | $F_M$4 | $F_M$ ≥ 2 | $F_M$4 | classification |
| IQR/M | ≤0.1 | 0.886 ± 0.024 | 0.937 ± 0.018 | 0.970 ± 0.011 | 77.1 | 90.4 | 69.1 |
| | 0.1< and ≥0.3 | 0.822 ± 0.015 | 0.868 ± 0.013 | 0.895 ± 0.015 | 75.6 | 84.7 | 62.6 |
| | >0.3 | 0.785 ± 0.035 | 0.842 ± 0.032 | 0.898 ± 0.031 | 69.1 | 80.6 | 53.9 |
| Comparison (p): | | | | | | | |
| Linear trend[b] | | — | — | — | 0.091 | 0.009 | 0.003 |
| ≤0.1 vs 0.1< and ≤0.3 | | 0.024 | 0.002 | <10⁻³ | 0.661 | 0.043 | 0.092 |
| ≤0.1 vs >0.3 | | 0.017 | 0.010 | 0.029 | 0.088 | 0.008 | 0.003 |
| 0.1< and ≤0.3 vs > 0.3 | | 0.331 | 0.451 | 0.931 | 0.081 | 0.196 | 0.039 |

[a]Rate of well-classified patients using 7.1 kPa as the LSE cut-off for the diagnosis of significant fibrosis ($F_M$ ≥ 2), 12.5 kPa for the diagnosis of cirrhosis ($F_M$4), or LSE classification ($F_{FS}0/1$, $F_{FS}2/3$, $F_{FS}4$) derived from the 2 previous diagnostic cut-offs (Castera et al);
[b]p for linear trend across the 3 subgroups of IQR/M LSE with 0.10<IQR/M≤0.30 had higher accuracy than LSE with IQR/M>0.30, but the difference did not reach statistical significance.

LSE median—By using 7.1 kPa as a diagnostic cut-off (Castera et al; Friedrich-Rust et al), the rate of well-classified patients for significant fibrosis was very good in LSE medians ≥7.1 kPa, but only fair in LSE medians <7.1 kPa: 81.5% vs 64.5%, respectively (p<10⁻³). By using 12.5 kPa as a diagnostic cut-off (Castera et al; Friedrich-Rust et al), the rate of well-classified patients for cirrhosis was excellent in LSE medians <12.5 kPa, but only fair in LSE medians ≥12.5 kPa: 94.3% vs 60.4%, respectively (p<10$^{-3}$). LSE thus demonstrated excellent negative predictive value for cirrhosis and very good positive predictive value for significant fibrosis. Conversely, it had insufficient positive predictive value for cirrhosis and insufficient negative predictive value for significant fibrosis. Finally, the rate of well-classified patients by the LSE classification derived from Castera et al. cut-offs was not significantly different among its 3 classes, $F_{FS}$0/1: 64.5%, $F_{FS}$2/3: 60.4%, and $F_{FS}$4: 60.4% (p=0.379).

TABLE 12

| | | LSE median | | Rate of |
|---|---|---|---|---|
| LSE diagnosis [a]: | <7.1 $F_{FS}$0/1 | 7.1≤-<12.5 $F_{FS}$2/3 | ≥12.5 $F_{FS}$4 | patients (%) |
| IQR/M ≤0.10 | | Very reliable LSE | | 16.6 |
| 0.10< and ≤0.30 | | Reliable LSE | | 74.3 [b] |
| >0.30 | | Poorly reliable LSE | | 9.1 |

[a] LSE diagnosis after categorization of LSE median into estimated Metavir F stages ($F_{FS}$) according to the diagnostic cut-offs of Castera et al.: 7.1 kPa for significant fibrosis and 12.5 kPa for cirrhosis (Castera et al);
[b] Including the subgroup with IQR/M > 0.30 and LSE median < 7.1

LSE accuracy in the subgroup of LSE with IQR/M≤0.10 was higher than in the whole population (Table 13).

TABLE 13

| | | | | Diagnostic accuracy (%)[a] | | |
|---|---|---|---|---|---|---|
| | AUROC | | | | | LSE |
| Diagnostic target: | $F_M$ ≥ 2 | $F_M$ ≥ 3 | $F_M$4 | $F_M$ ≥ 2 | $F_M$4 | classification |
| LSE: | | | | | | |
| All[b] | 0.822 ± 0.012 | 0.872 ± 0.010 | 0.910 ± 0.011 | 74.9 | 85.0 | 62.4 |
| Very reliable | 0.886 ± 0.024 | 0.937 ± 0.018 | 0.970 ± 0.011 | 77.1 | 90.4 | 69.1 |
| Reliable | 0.823 ± 0.014 | 0.876 ± 0.012 | 0.904 ± 0.014 | 75.3 | 85.8 | 63.2 |
| Poorly reliable | 0.773 ± 0.045 | 0.745 ± 0.049 | 0.819 ± 0.052 | 67.6 | 69.5 | 43.8 |
| Comparison (p): | | | | | | |
| Linear trend[c] | — | — | — | 0.107 | <10$^{-3}$ | <10$^{-3}$ |
| Very reliable vs reliable | 0.023 | 0.005 | <10$^{-3}$ | 0.603 | 0.090 | 0.125 |
| Very reliable vs poorly reliable | 0.027 | <10$^{-3}$ | 0.004 | 0.076 | <10$^{-3}$ | <10$^{-3}$ |
| Reliable vs poorly reliable | 0.289 | 0.009 | 0.115 | 0.088 | <10$^{-3}$ | <10$^{-3}$ |

Figure 5:
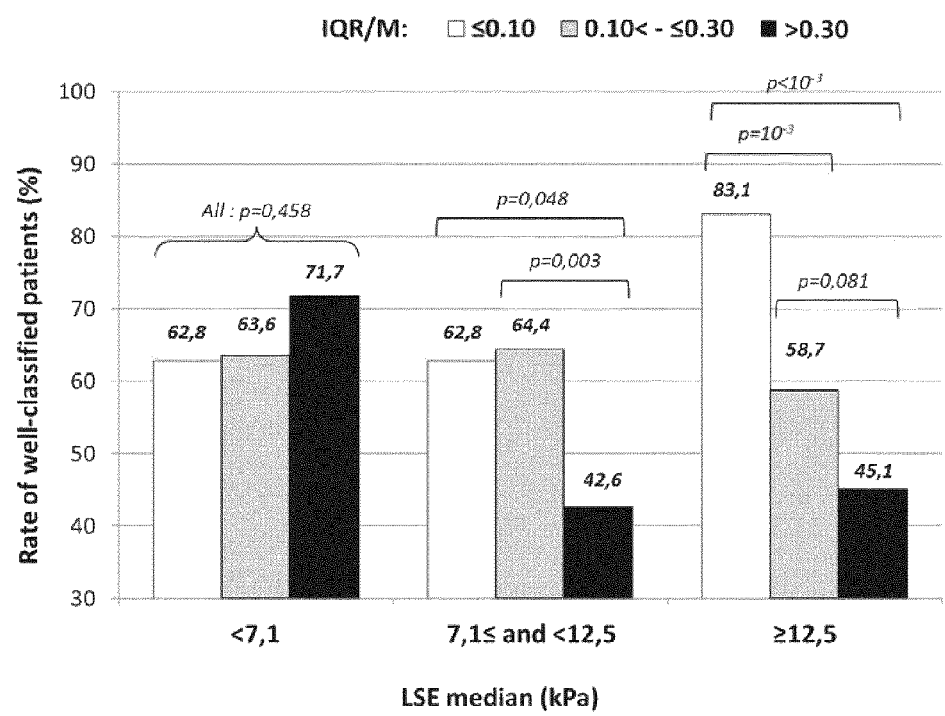
FIG. 5 is a graph showing the rate of well-classified patients by the liver stiffness evaluation (LSE) classification derived from Castera et al. cut-offs, as a function of the 3 classes of the classification and IQR/M, showing that IQR/M is a good predictor of reliability.
Figure 6:
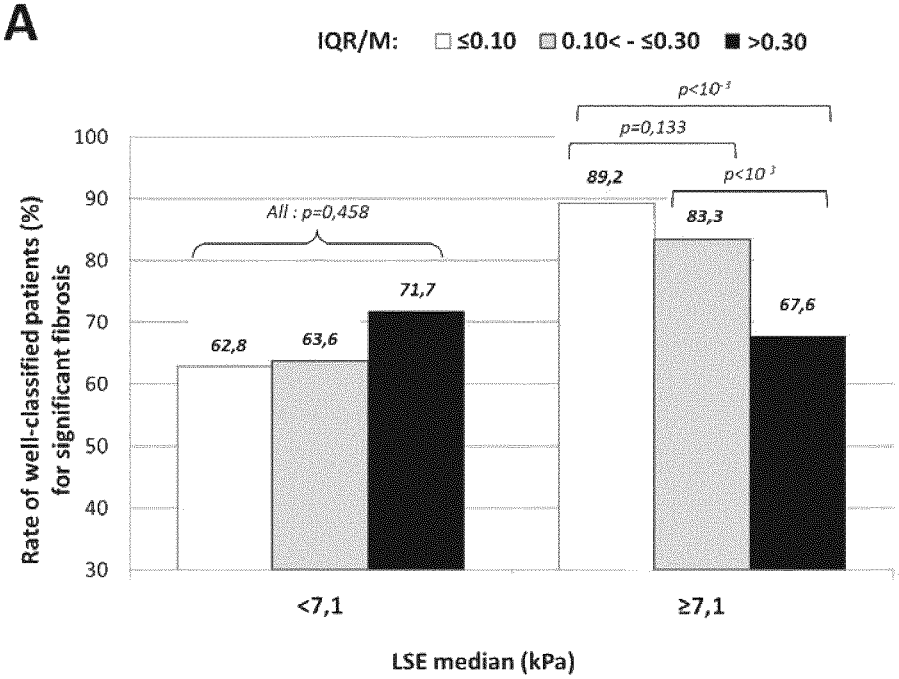
FIG. 6 is a combination of graphs showing the rate of well-classified patients by LSE for the diagnosis of (A) significant fibrosis (diagnostic cut-off: 7.1 kPa), or (B) cirrhosis (diagnostic cut-off: 12.5 kPa) as a function of LSE median and IQR/M.
Figure 6:
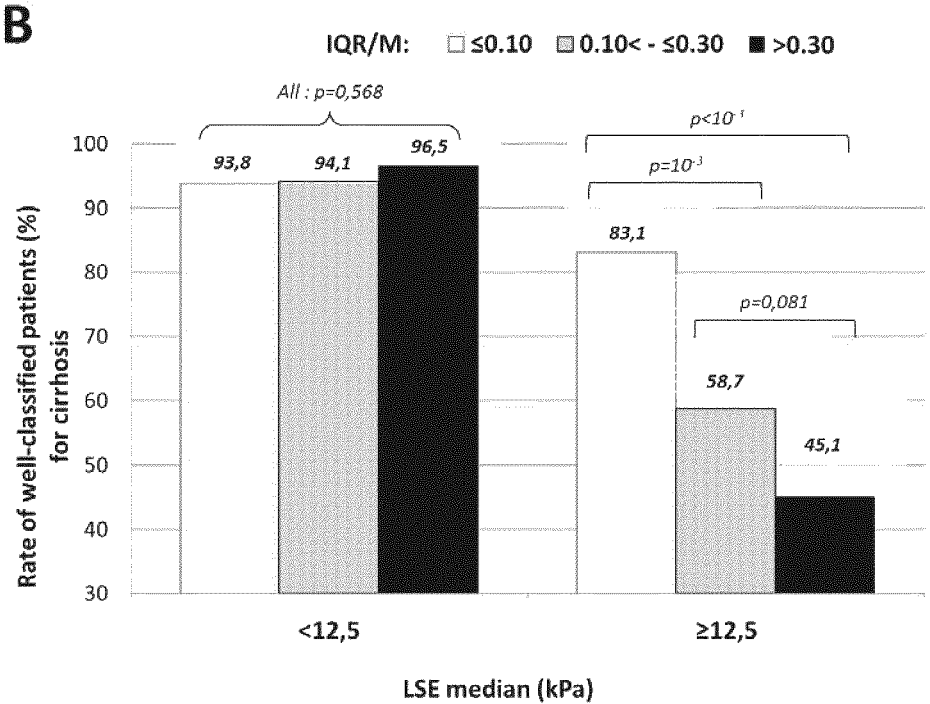

[a] Rate of well-classified patients using 7.1 kPa as the LSE cut-off for the diagnosis of significant fibrosis ($F_M$ ≥ 2), 12.5 kPa for the diagnosis of cirrhosis ($F_M$4), or LSE classification ($F_{FS}$0/1, $F_{FS}$2/3, $F_{FS}$4) derived from the 2 previous diagnostic cut-offs (Castera et al);
[b] This result, already presented in table 2, is provided here for comparison with subgroups;
[c] p for linear trend across the 3 subgroups of LSE IQR/M and LSE median—In patients with LSE median <7.1 kPa, the diagnostic accuracy of the LSE classification derived from Castera et al. cut-offs was not significantly different among the three IQR/M subgroups (p=0.458; FIG. 5). Conversely, in patients with LSE median ≥7.1 kPa, the diagnostic accuracy of the LSE classification was significantly lower in LSE with IQR/M>0.30 compared to LSE with IQR/M≤0.30 (43.8% vs 64.1%, p<10$^{-3}$; FIG. 5). The rates of well-classified patients for the binary diagnoses of significant fibrosis or cirrhosis as a function of IQR/M and LSE median are detailed in FIG. 6. Briefly, in patients with LSE median ≥7.1 kPa, LSE with IQR/M>0.30 had lower accuracy for significant fibrosis than LSE with IQR/M≤0.30 (67.6% vs 84.3%, p<10$^{-3}$). In patients with LSE median ≥12.5 kPa, LSE with IQR/M>0.30 had lower accuracy for cirrhosis than LSE with IQR/M≤0.30 (45.1% vs 64.0%, p=0.011).

Proposal for New Reliability Criteria in LSE

The previous findings led us to develop new criteria for the interpretation of LSE results (Table 12).

LSE in this subgroup were thus considered as "very reliable". LSE with 0.10<IQR/M≤0.30 or with IQR/M>0.30 and LSE median<7.1 kPa provided accuracy similar to that of the whole population and were thus considered as "reliable". Finally, LSE with IQR/M>0.30 and LSE median≥7.1 kPa provided accuracy lower than that of the whole population and were thus considered as "poorly reliable". Thresholds were determined as a function of literature data and/or classical statistical techniques for cut-off determination. LSE accuracy in the subgroup of LSE with IQR/M≤0.10 was higher than in the whole population. LSE in this subgroup were thus considered as "very reliable". LSE with 0.10<IQR/M≤0.30 or with IQR/M>0.30 and LSE median<7.1 kPa provided accuracy similar to that of the whole population and were thus considered as "reliable". Finally, LSE with IQR/M>0.30 and LSE median ≥7.1 kPa provided accuracy lower than that of the whole population and were thus considered as "poorly reliable".

According to these new criteria, 16.6% of LSE were considered as "very reliable", 74.3% as "reliable", and 9.1% as "poorly reliable". Importantly, LSE AUROCs and diagnostic accuracies were significantly different among these 3 subgroups (Table 13). Finally, the rate of poorly reliable LSE according to the new criteria was significantly lower than that of unreliable LSE according to the usual definition (9.1% vs 24.3%, $p<10^{-3}$).

Sensitivity Analysis

We evaluated our new criteria for LSE reliability as a function of several potential influencing characteristics: cause of liver disease (CHC vs. others), diagnostic indexes (AUROC, binary diagnosis of significant fibrosis or cirrhosis, LSE classification), and diagnostic cut-offs published by Ziol et al., Stebbing et al., and Friedrich-Rust et al. Briefly, whatever the potential influencing factor, a decrease in LSE reliability, according to our new criteria, was associated with a decrease in LSE accuracy. BMI (<25 vs ≥25 kg/m$^2$) did not influence LSE accuracy in any of the 3 new categories of LSE reliability. Because of the few numbers of patients with hepatitis B, alcohol abuse, or NAFLD, it was not possible to perform a sensitivity analysis for these causes of chronic liver disease.

The invention claimed is:

1. A method for improving the reliability of a non-invasive diagnostic test of the presence and/or the severity of a liver disease, said method comprising:
   a. collecting a diagnostic Initial Index, by way of the sub-steps of:
      i. carrying out a blood test, said test being a test derived from the FibroMeter Family where urea was deleted from the markers, by measuring in a blood sample obtained from a subject the markers combined in a test of the FibroMeter Family, minus urea,
      ii. carrying out a Fibroscan™ in said subject, resulting in a liver or spleen elastometry data, and
      iii. mathematically combining the data resulting from the measure of the blood test markers with the liver or spleen elastometry data resulting from the Fibroscan™,
   thereby collecting the Initial Index;
   b. analyzing the reliability of each data mathematically combined to collect the Initial Index by identifying if at least one data of the Initial Index collected in step a) is any of an abnormal data, an inconsistent data, and a non-homogeneous data, or is responsible for a greater decrease in a Dispersion Index than that observed with other data:
      i. with comparison of each data to an expected data in the reference population, or
      ii. in view of intrinsic or extrinsic reliability predictor(s), or
      iii. by calculating the Dispersion Index of the Initial Index collected in step a), a high Dispersion Index meaning homogeneous data of the Initial Index, and performing a series of calculations of the Dispersion Index of the Initial Index comprising n data where 1 to (n−2) data of the Initial Index are deleted, resulting in ranking the data lowering the most the Dispersion Index; or
   analyzing the reliability of the Initial Index by positioning the Initial Index in a reliability class of a reliability classification based on the data obtained in a reference population;
   c. if a data is an abnormal, inconsistent and/or non-homogeneous data, or a data lowering a Dispersion Index, generating an Event Alert;
   d. if an Event Alert is generated, calculating new indexes, where the abnormal, inconsistent and/or non-homogeneous data, or the data responsible for a lowest Dispersion Index, is suppressed thereby obtaining an Alternative Index; or where the abnormal, inconsistent or non-homogeneous data, or the data responsible for the lowest Dispersion Index is substituted by its mean value thereby obtaining an Estimated Index; or, if at least two data are abnormal, inconsistent or non-homogeneous, or the data responsible for the lowest Dispersion Index, a most discordant of the at least two data is suppressed and the other(s) of the at least two data is/are substituted by its/their mean value thereby obtaining a Mixed Index;
   e. replacing the Initial Index comprising an abnormal, inconsistent and/or a non-homogeneous data or a data affecting the Dispersion Index, with the Alternative Index, the Estimated Index, or the Mixed Index.

2. The method according to claim 1, wherein:
   in step b) the reliability of each data combined to collect the Initial Index is analyzed through the calculation of the Dispersion Index of the Initial Index collected in step a), thereby identifying which is the data of the Initial Index collected in step a) most decreasing the Dispersion Index, by performing a series of calculations of Dispersion Index of the Initial Index comprising n data where 1 to (n−2) data of the Initial Index are deleted; and
   in step e), the Initial Index comprising a data lowering the most the Dispersion Index is replaced with an Alternative Index where the data lowering the Dispersion Index is deleted.

3. The method according to claim 1, wherein step c) is performed after having calculated if the Dispersion Index of the Initial Index corresponds to the ones of the $2^{nd}$ to $9^{th}$ deciles, of a population of reference.

4. The method according to claim 1, wherein when a data is an abnormal data, the Event Alert is an Abnormal Data Alert; when a data is an inconsistent data, the Event Alert is an Inconsistent Data Alert; when a data is a non-homogeneous data, the Event Alert is a Non-Homogeneous Data Alert.

5. The method according to claim 1,
   wherein the Event Alerts generated in step c) are preliminary analyzed, prior to step d), and
   wherein said treatment comprises:
      the suppression of one or more Event Alert(s) when the data having triggered the Event Alert is found reliable, and/or
      when several Event Alerts are issued, the prioritization of said Event Alerts to identify a main Event Alert according to its impact on Initial Index.

6. The method according to claim 1, wherein reliability predictors are selected from the group comprising urea, ALT, AST, CirrhoMeter$^{2G}$ score, FibroMeter$^{2G}$ score, Fibroscan™ classes, FibroMeter™ classes, CirrhoMeter™ classes, Fibroscan™ median, IQR, IQR/M, platelets, A2M, ratio urea/ Fibroscan and Dispersion Index of the Initial Index.

7. The method according to claim 1, wherein in step b):
   the reliability of each data combined to collect the Initial Index is analyzed
      with comparison of each data to the expected data in the reference population, or
      in view of intrinsic or extrinsic reliability predictor(s), thereby identifying if at least one data of the Initial Index collected in step a) is an abnormal data, inconsistent data, and/or non-homogeneous data.

8. The method according to claim 1, wherein in step b) the reliability of an Initial Index is determined by positioning said Index in a reliability class of a reliability classification including a two-entry table of Explained Data and Explanatory Data, established on the basis of a population of reference, wherein the reading of the position of the Index in the table gives the reliability of the Index with consideration to the Explanatory Data.

9. The method according to claim 1, wherein, in step e), there is further included a sub-step of replacing the Initial Index with the most reliable index selected from the group consisting of an Alternative Index, an Estimated Index, or a Mixed Index.

10. An expert system implementing the method according to claim 1.

11. A software implementing the method according to claim 1.

* * * * *